US012741005B2

(12) United States Patent
Cavaleri

(10) Patent No.: US 12,741,005 B2
(45) **Date of Patent: *Sep. 22, 2026**

(54) WITHANOLIDE-ENRICHED COMPOSITIONS AND METHODS OF USE THEREOF

(71) Applicant: Franco Cavaleri, Surrey (CA)

(72) Inventor: Franco Cavaleri, Surrey (CA)

( * ) Notice: Subject to any disclaimer, the term of this patent is extended or adjusted under 35 U.S.C. 154(b) by 411 days.

This patent is subject to a terminal disclaimer.

(21) Appl. No.: 18/272,015

(22) PCT Filed: Jan. 13, 2022

(86) PCT No.: PCT/CA2022/050048

§ 371 (c)(1),
(2) Date: Jul. 12, 2023

(87) PCT Pub. No.: WO2022/150918

PCT Pub. Date: Jul. 21, 2022

(65) Prior Publication Data

US 2024/0082339 A1 Mar. 14, 2024

Related U.S. Application Data

(63) Continuation-in-part of application No. 17/495,855, filed on Oct. 7, 2021, now abandoned.

(60) Provisional application No. 63/137,358, filed on Jan. 14, 2021.

(51) Int. Cl.
*A61K 36/81* (2006.01)
*A61K 31/585* (2006.01)
*A61P 17/14* (2006.01)

(52) U.S. Cl.
CPC ............ *A61K 36/81* (2013.01); *A61K 31/585* (2013.01); *A61P 17/14* (2018.01)

(58) Field of Classification Search
CPC ........ A61K 36/81; A61K 31/585; A61P 17/14
See application file for complete search history.

(56) References Cited

U.S. PATENT DOCUMENTS

| | | | | |
|---|---|---|---|---|
| 7,108,870 | B2 * | 9/2006 | Sangwan | A61K 36/81 514/453 |
| 10,709,659 | B1 * | 7/2020 | Morley | A61K 8/735 |
| 2011/0236324 | A1 | 9/2011 | Deo | |

FOREIGN PATENT DOCUMENTS

| | | |
|---|---|---|
| IN | 201911034479 | 6/2019 |
| WO | WO2004/050015 | 6/2004 |
| WO | WO2017/068600 | 4/2017 |
| WO | WO2020/079712 | 4/2020 |

OTHER PUBLICATIONS

Pandey, M., et al., Preparation and evaluation of hair growth formulations of Indian ginseng (Withania somnifera ) for alopecia, 2019 , Asian J Biol Sci, 12(3):524-532, 10 pages. <https://scialert.net/abstract/?doi=ajbs.2019.524.532>. (Year: 2019).*

Kuang Z, Bai J, Ni L, Hang K, Xu J, Ying L, Xue D, Pan Z. Withanolide B promotes osteogenic differentiation of human bone marrow mesenchymal stem cells via ERK1/2 and Wnt/β-catenin signaling pathways. Int Immunopharmacol. Nov. 2020;88:106960. doi: 10.1016/j.intimp.2020.106960. Epub Sep. 9, 2020. (Year: 2020).*

Nile SH, Nile A, Gansukh E, Baskar V, Kai G. Subcritical water extraction of withanosides and withanolides from ashwagandha ( Withania somnifera L) and their biological activities. Food Chem Toxicol. Oct. 2019;132:110659. doi: 10.1016/j.fct.2019.110659. Epub Jul. 2, 2019. PMID: 31276745. (Year: 2019).*

Suman S, Das TP, Sirimulla S, Alatassi H, Ankem MK, Damodaran C. Withaferin-A suppress AKT induced tumor growth in colorectal cancer cells. Oncotarget. Mar. 22, 2016;7(12):13854-64. doi: 10.18632/oncotarget.7351. PMID: 26883103; PMCID: PMC4924683. (Year: 2016).*

Grogan PT, et al. Cytotoxicity of withaferin A in glioblastomas involves induction of an oxidative stress-mediated heat shock response while altering Akt/mTOR and MAPK signaling pathways. Invest New Drugs. Jun. 2013;31(3):545-57. doi: 10.1007/s10637-012-9888-5. Epub Nov. 6, 2012. PMID: 23129310. (Year: 2013).*

Heyninck, K. et al., "Withaferin A induces heme oxygenase (HO-1) expression in endothelial cells via activation of the Keap1/Nrf2 pathway," Biochemical Pharmacology, Apr. 1, 2016 (Jan. 4, 2016), vol. 109, pp. 48-61.

Third Party Observation for PCT/CA2022/050048.

Hogan et al. (J. Surfactants Deterg .; 2020).

* cited by examiner

*Primary Examiner* — Aaron J Kosar
*Assistant Examiner* — Jennifer Lynn Cain

(57) ABSTRACT

Compositions that contain enriched amounts of Withanolides are provided. Such compositions will include, consist essentially of, or consist entirely of natural extracts of Ashwagandha (*Withania somnifera*), including whole plant extracts and/or root extracts, which have been supplemented with additional amounts of Withanolide A, Withanolide B, Withanolide D, Withaferin A, Withanoside IV, and/or Withanoside V. The additional amounts of such Withanolides that are added to the Ashwagandha extracts may be naturally occurring isolates or synthetic versions of such Withanolides, such that the total/final Withanolide concentration is at least ten (10%)(w/w)—but may include even higher concentrations of such Withanolides. Methods for modulating GPX1, Nrf2, HO1, mTOR, TERT, β-Catenin, and/or NF-$_{K}$B using such Withanolide-enriched compositions are also disclosed.

5 Claims, 21 Drawing Sheets

$IC_{50}$ = 0.4mM

WITHANOLIDE-ENRICHED COMPOSITIONS AND METHODS OF USE THEREOF

CROSS-REFERENCE TO RELATED APPLICATIONS

This application is a national stage patent application under 35 U.S.C. 371 of PCT Patent Application PCT/CA2022/050048, filed on Jan. 13, 2022, which claims priority to, and incorporates by reference, U.S. patent application Ser. No. 17/495,855, filed on Oct. 7, 2021, which claims priority to U.S. provisional patent application 63/137,358, filed on Jan. 14, 2021.

FIELD OF THE INVENTION

The field of the present invention generally relates to certain concentrated forms of Withanolides (and methods of use thereof), which can be used to target and/or modulate a variety of biomarkers. Such biomarkers include, for example, GPX1, Nrf2, HO1, mTOR, TERT, β-Catenin, and/or NF-$_K$B. In addition, the field of the present invention relates to the use of such Withanolide-enriched compositions to reduce and/or mitigate the effects of oxidative stress within a group of cells. Still further, the field of the present invention relates to the use of such Withanolide-enriched compositions to treat and/or prevent various health conditions associated with such biomarkers and/or oxidative stress. The field of the present invention further relates to certain Withanolide-enriched compositions for induction of autophagy within hair follicle cells and for reactivating dormant hair follicle cells to facilitate the growth and regeneration of such cells.

BACKGROUND OF THE INVENTION

The mammalian target of rapamycin (mTOR) is a serine/threonine-specific protein kinase that belongs to the family of phosphatidylinositol-3 kinases (PI3K). mTOR has been shown to regulate cellular metabolism, growth, and proliferation by forming and signaling through two protein complexes, namely, mTORC1 and mTORC2. Over the years, a number of compositions have been developed that modulate mTOR activity, which have further been shown to exhibit certain anti-cancer activity in clinical trials (against various types of tumors).

Another known anti-cancer target is nuclear factor kappa-light-chain-enhancer of activated B cells, which is commonly known as NF-$_K$B. NF-$_K$B is a protein complex that controls transcription of DNA, cytokine production, and cell survival. Similar to mTOR, it has been found that modulating and, in some cases, inhibiting NF-$_K$B expression and/or activity may have certain beneficial anti-cancer effects, as well as reduce inflammation and stress (and possibly prevent or slow the progression of Alzheimer's Disease).

Although currently-available modulators of mTOR and/or NF-$_K$B have demonstrated some modicum of success and efficacy, a continuing need exists for improved compositions for inhibiting such targets—and preventing, treating, and/or ameliorating the effects of various cancers, inflammation, stress, and Alzheimer's Disease. In addition, compositions that modulate mTOR could also be used to induce autophagy within hair follicle cells and thereby encourage the reactivation and growth of dormant hair follicle cells.

The present invention, as described further below, addresses many of such demands in the marketplace.

SUMMARY OF THE INVENTION

According to certain aspects of the present invention, compositions that contain enriched amounts of Withanolides are provided, e.g., compositions that include enriched and elevated levels of Withanolide A, Withanolide B, Withanolide D, Withaferin A, Withanoside IV, Withanoside V, and combinations thereof. More particularly, compositions that comprise, consist essentially of, or consist entirely of natural extracts of Ashwagandha (*Withania somnifera*), including whole plant extracts, root extracts, leaf extracts, or a combination of such extracts, which have been supplemented with additional amounts of purified Withanolide A, Withanolide B, Withanolide D, Withaferin A, Withanoside IV, and/or Withanoside V are provided.

In certain embodiments, the invention provides that the compositions will comprise, consist essentially of, or consist entirely of such natural extracts of Ashwagandha (*Withania somnifera*), which further includes additional amounts of purified (or substantially purified) Withanolide A, Withanolide B, Withanolide D, Withaferin A, Withanoside IV, and/or Withanoside V (whether naturally-occurring isolates or synthetic versions thereof), such that the total Withanolide concentration is preferably at least ten percent (10%) (w/w) of the total Ashwagandha extract, for compositions intended for oral consumption/administration—but, as described further herein, may include even higher concentrations of Withanolides. More particularly, in certain preferred embodiments, such compositions intended for oral consumption/administration may comprise 10%-15% (w/w) total Withanolides, with Withaferin A being present in a range between 1%-1.5% (w/w), of the total Ashwagandha extract. For compositions intended for scalp application (as described further below), the total Withanolide concentration is preferably at least thirty five percent (35%) (w/w) of the total Ashwagandha extract. More particularly, in certain preferred embodiments, such compositions intended for scalp or general skin (topical) application may comprise 35%-40% (w/w) total Withanolides, with Withaferin A being present in a range between 20%-30% (w/w), of the total Ashwagandha extract.

According to additional aspects of the present invention, methods for modulating various biological targets using such Withanolide compositions are provided, such as GPX1, Nrf2, HO1, mTOR, TERT, β-Catenin, and/or NF-$_K$B expression and/or activity in a group of cells (and/or within human subjects) are provided. Similarly, methods for preventing, treating, and/or ameliorating the effects of various cancers, inflammation, stress (including oxidative stress), premature aging and Alzheimer's Disease are provided, which generally entail administering an effective amount of a Withanolide-enriched composition described herein.

According to yet further aspects of the present invention, methods of using the concentrated forms of Withanolides described herein for induction of autophagy within hair follicle cells are provided. The invention provides that such methods may be utilized for (a) increasing and inducing the anagen growth phase of hair follicles and (b) reactivating dormant hair follicle cells to facilitate the growth and regeneration of such cells. Such aspects of the present invention further include concentrated forms of Withanolides formulated for topical scalp applications.

The above-mentioned and additional features of the present invention are further illustrated in the Detailed Description contained herein.

DETAILED DESCRIPTION OF THE INVENTION

Figure 1:
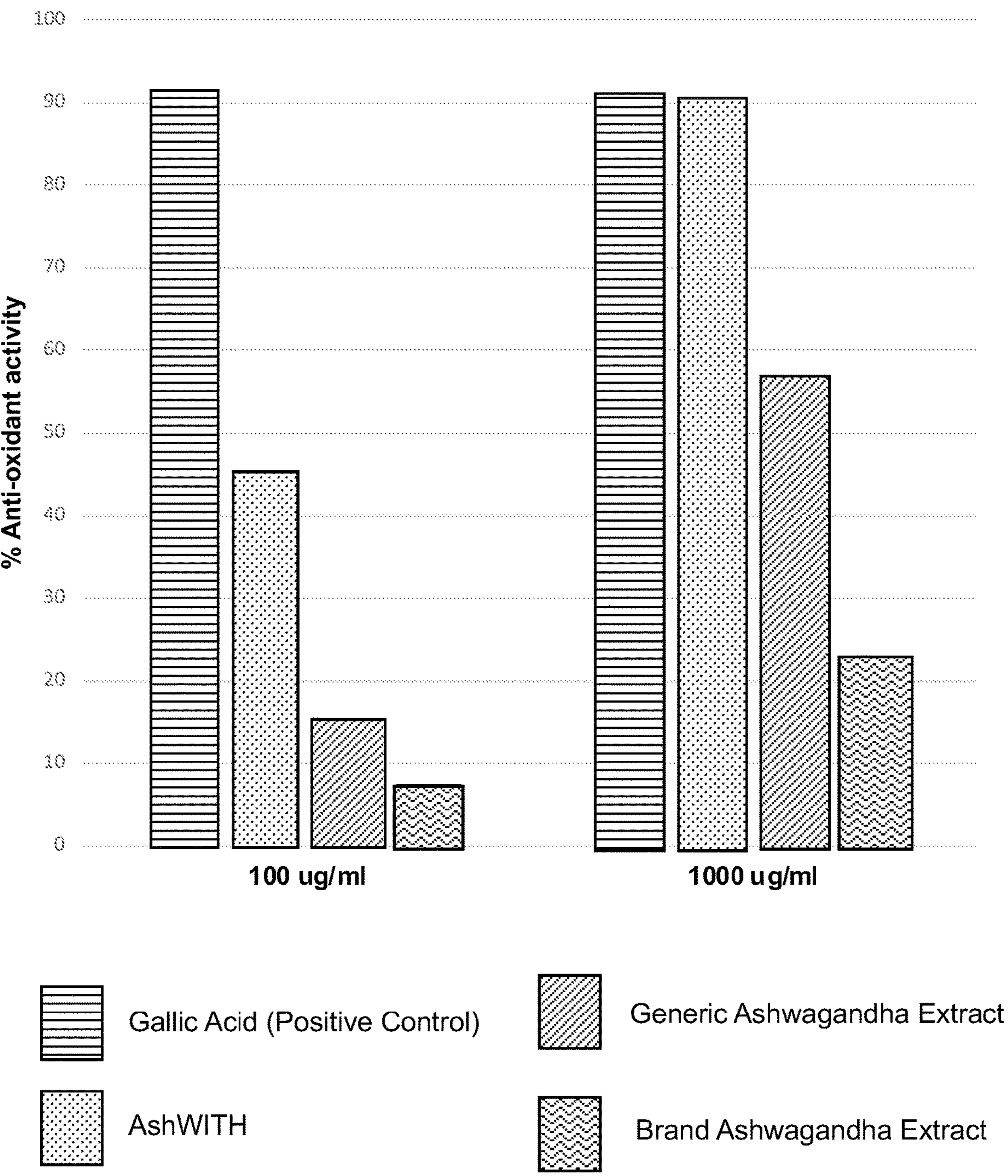
FIG. 1 is a bar graph that summarizes the anti-oxidant potentials of gallic acid; generic and brand Ashwagandha extracts; and the Ashwagandha/Withanolide-enriched compositions of the present invention.

The following will describe, in detail, several preferred embodiments of the present invention. These embodiments are provided by way of explanation only, and thus, should not unduly restrict the scope of the invention. In fact, those of ordinary skill in the art will appreciate upon reading the present specification and viewing the present drawings that the invention teaches many variations and modifications, and that numerous variations of the invention may be employed, used and made without departing from the scope and spirit of the invention.

According to certain preferred embodiments of the present invention, compositions that include enriched amounts of Withanolides are provided. More particularly, compositions that comprise, consist essentially of, or consist entirely of natural extracts of the plant Ashwagandha (*Withania somnifera*), including whole plant extracts, root extracts, leaf extracts, or a combination of such extracts, which have been supplemented with additional amounts of purified (or substantially purified) Withanolide A, Withanolide B, Withanolide D, Withaferin A, Withanoside IV, and/or Withanoside V are provided.

Withanolide A is a steroidal lactone, derived from *Withania somnifera* (and other members of the Solanaceae family). Withanolide A is also referred to as (5α,6α,7α,22R)-6,7-Epoxy-5,20,22-trihydroxy-1-oxo-ergosta-2,24-dien-26-oic acid δ-lactone, and is represented by the following structure:

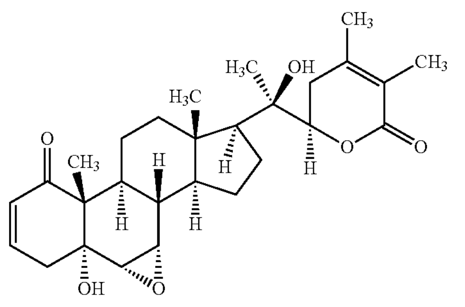

Withanolide B is a steroidal lactone, derived from *Withania somnifera* (and other members of the Solanaceae family). Withanolide B is also referred to as (5α,6α,7α,22R)-6,7-Epoxy-5,22-dihydroxy-1-oxo-ergosta-2,24-dien-26-oic acid δ-lactone, and is represented by the following structure:

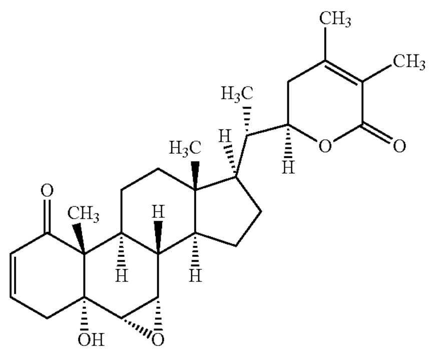

Withanolide D is a steroidal lactone, derived from *Withania somnifera* (and other members of the Solanaceae family). Withanolide D is also referred to as 5,6-Epoxy-4,20,22-trihydroxy-1-oxoergosta-2,24-dien-26-oic acid delta-lactone, and is represented by the following structure:

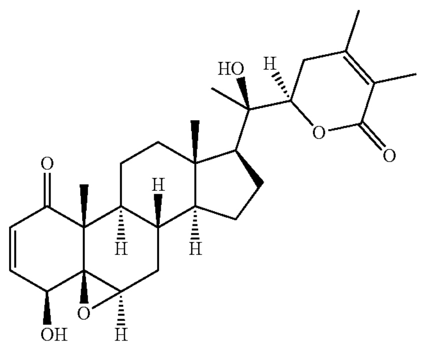

Withaferin A is a steroidal lactone, derived from *Withania somnifera* (and other members of the Solanaceae family). Withaferin A is also referred to as (4β,5β,6β,22R)-4,27-Dihydroxy-5,6:22,26-diepoxyergosta-2,24-diene-1,26-dione, and is represented by the following structure:

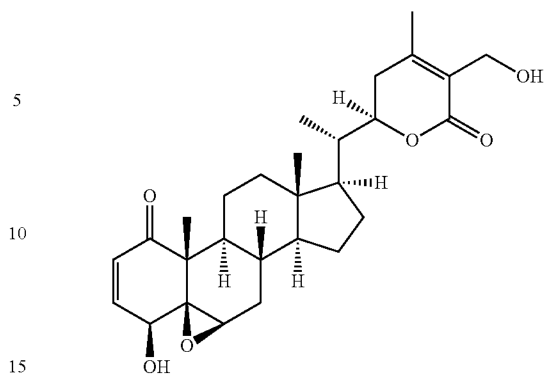

Withanoside IV is a steroidal lactone, derived from *Withania somnifera* (and other members of the Solanaceae family). Withanoside IV is also referred to as (1α,3β,22R)-3-[(6-O-β-D-Glucopyranosyl-β-D-glucopyranosyl)oxy]-1,22,27-trihydroxy-ergosta-5,24-dien-26-oic acid δ-lactone, and is represented by the following structure:

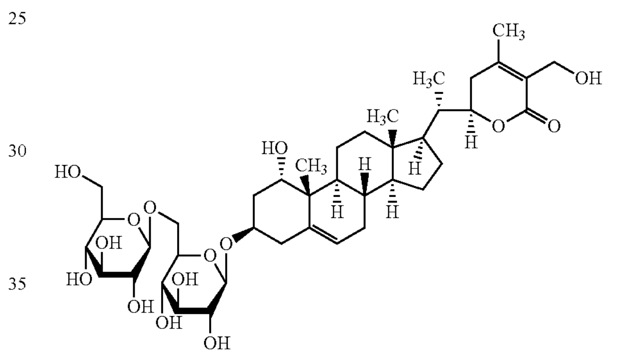

Withanoside V is a steroidal lactone, derived from *Withania somnifera* (and other members of the Solanaceae family). Withanoside V is also referred to as (1α,3β,22R)-3-[(6-O-β-D-Glucopyranosyl-β-D-glucopyranosyl)oxy]-1,22-dihydroxy-ergosta-5,24-dien-26-oic acid δ-lactone, and is represented by the following structure:

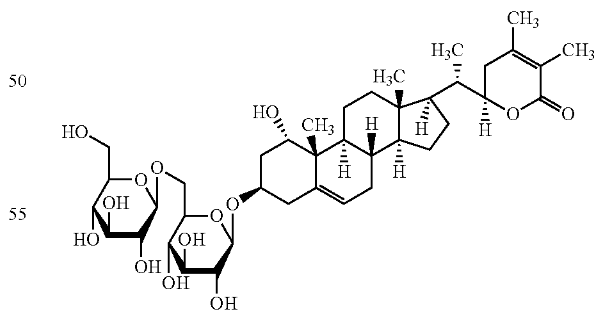

In certain preferred embodiments, the present invention provides that the compositions will comprise, consist essentially of, or consist entirely of such natural extracts of Ashwagandha (*Withania somnifera*)(including whole plant extracts, root extracts, leaf extracts, or a combination of such extracts), which further includes additional amounts of one or more of the Withanolides described herein (whether purified naturally-occurring isolates or synthetic versions thereof), such that the total Withanolide concentration is at least ten (10%)(w/w) of the Ashwagandha extract. More particularly, the compositions of the present invention include natural extracts of Ashwagandha, which have been supplemented with additional Withanolides, such that the final concentration of Withanolides in the composition exceeds the concentration that is naturally-occurring in Ashwagandha extracts. For example, the composition of the present invention may include elevated amounts of one or more of the Withanolides described herein, such that the final concentration of all Withanolides is at least 10% (w/w), or at least 15% (w/w), or at least 20% (w/w), or at least 25% (w/w), or at least 30%, 40%, 50%, 60%, 70%, 80%, or 90% (w/w) of the Ashwagandha extract—such that, other than the Withanolides, the balance of the composition consists essentially of (or consisting entirely of) natural extracts of Ashwagandha (*Withania somnifera*), including whole plant extracts, root extracts, leaf extracts, or a combination of such extracts.

The present invention encompasses two preferred embodiments. In a first preferred embodiment, the composition includes no less than 10% (w/w) total Withanolides and no more than 1.5% (w/w) Withaferin A. More particularly, in this embodiment, a natural extract of Ashwagandha is supplemented with additional Withaferin A, such that the resulting composition includes no less than 10% (w/w) total Withanolides and no more than 1.5% (w/w) Withaferin A, relative to the total modified natural extract of Ashwagandha. More particularly, in certain preferred embodiments, such compositions intended for oral consumption/administration may comprise 10%-15% (w/w) total Withanolides, with Withaferin A being present in a range between 1%-1.5% (w/w), of the total Ashwagandha extract. Such composition may then, optionally, be combined with fillers, carriers, solvents, etc., to formulate a composition for oral consumption, as described further below.

In a second preferred embodiment, the composition includes no less than 35% (w/w) total Withanolides and no less than 20% (w/w) Withaferin A or, in some embodiments, no less than 25% (w/w) Withaferin A. More particularly, in this embodiment, a natural extract of Ashwagandha is supplemented with additional Withaferin A, such that the resulting composition includes no less than 35% (w/w) total Withanolides and no less than 25% (w/w) Withaferin A, relative to the total modified natural extract of Ashwagandha. Still more particularly, in certain preferred embodiments, such compositions intended for scalp application may comprise 35%-40% (w/w) total Withanolides, with Withaferin A being present in a range between 20%-30% (w/w), of the total Ashwagandha extract. Such composition may then, optionally, be combined with fillers, carriers, solvents, surfactants, etc., to formulate a composition for scalp administration, as described further below.

As mentioned above, the additional Withanolides that are added to the Ashwagandha (*Withania somnifera*) extract may consist of natural/concentrated forms of Withanolides (i.e., Withanolide isolates). Alternatively, the Withanolides that are added to the Ashwagandha (*Withania somnifera*) extract may consist of chemically-synthesized Withanolides. In addition, as mentioned above, the Ashwagandha (*Withania somnifera*) extract into which the additional Withanolides are added may consist of whole plant extract or, in other embodiments, root extract alone, leaf extracts, or a combination of such extracts.

The invention provides that the Ashwagandha (*Withania somnifera*) extracts used to formulate the compositions of the present invention may be sourced from commercial vendors. In other embodiments, known methods may be employed for producing such extracts. For example, dried Ashwagandha (*Withania somnifera*)—whole plant or roots—may be suspended within an alcohol solvent, e.g., suspended in 85% ethanol at a ratio of 1:30 and subsequently incubated at 85-degrees Celsius for 2 hours in a reflux system. The refluxed extract may then be filtered and concentrated via evaporation at 60-degrees Celsius. The filtrate may then be lyophilized (subjected to a freeze-drying process) overnight—and later reconstituted using an appropriate solvent/buffer, such as an aqueous buffer.

According to additional preferred embodiments of the present invention, methods for modulating the expression and/or activity of GPX1, Nrf2, HO1, mTOR, TERT, β-Catenin, and/or NF-$_K$B in a group of cells are provided—and, in some embodiments, methods for increasing the expression and/or activity of GPX1, Nrf2, HO1, mTOR, TERT, β-Catenin, and/or NF-$_K$B in a group of cells are provided. Such methods generally include providing to a group of cells, either directly or indirectly, an effective amount of the Withanolide-enriched compositions described herein. Successful modulation of such targets allows for indications related to cell preservation, cell protection, cellular antioxidant enhancement, cell protection from oxidation and inflammation, countermeasures against premature aging, and enhancement or activation of hair follicle activity and functionality.

According to yet further related embodiments of the present invention, methods for preventing and/or ameliorating the effects of certain diseases associated with GPX1, Nrf2, HO1, mTOR, TERT, β-Catenin, and/or NF-$_K$B are provided. Such methods generally include providing to a subject an effective amount of the Withanolide-enriched compositions described herein. Non-limiting examples of such diseases include various cancers, inflammation, stress (including oxidative stress), anxiety, alopecia, and Alzheimer's Disease. In such embodiments, the "effective amount" of a Withanolide-enriched composition will preferably be sufficient to significantly modulate and alter GPX1, Nrf2, HO1, mTOR, TERT, β-Catenin, and/or NF-$_K$B expression levels (such as by at least 10% relative to a control cell line or, even more preferably, by at least 20% relative to a control cell line).

According to additional embodiments of the present invention, methods for inhibiting PDE5; preventing and/or ameliorating the effects of erectile dysfunction; improving sexual performance, activity, and interest; modulating Nrf2 and inducing CAT, SOD, and glutathione peroxidase activity (for the treatment of cellular/oxidative stress); modulating heme oxygenase (HO); modulating glutathione peroxidase (GSH); modulating enhancing mitochondrial activity and health (by modulating proton gradients); and inhibition of stress-related adipocyte differentiation are provided. Such methods generally include providing to a subject an effective amount of the Withanolide-enriched compositions described herein.

In yet additional embodiments of the present invention, the Withanolide-enriched compositions may further include and/or be added to various formulations that are designed for human administration. For example, according to certain additional embodiments, the present invention encompasses therapeutic compositions (and methods of use thereof) that include a Withanolide-enriched Ashwagandha extract of the present invention, which consists of at least 10% (w/w) Withanolides relative to the Ashwagandha extract (although such compositions may, in certain embodiments, include at least 15%, 20%, 30%, 40%, 50%, 60%, 70%, 80%, or 90% (w/w) Withanolides), relative to the Ashwagandha (*Withania somnifera*) extract described herein. Still further, in certain preferred embodiments, the Withanolide-enriched therapeutic Ashwagandha extract will include no more than 1.5% (w/w) Withaferin A. Such Withanolide-enriched Ashwagandha extract may then be combined with a pharmaceutically acceptable solvent, filler, or carrier, as described herein.

The invention provides that the therapeutic compositions described herein may be administered in any desired and effective manner, e.g., as pharmaceutical compositions or nutritional supplements for oral ingestion. More particularly, for example, pharmaceutically acceptable compositions or nutritional supplements of the invention may comprise one or more of the compositions described herein with one or more acceptable carriers. Regardless of the route of administration selected, the compositions may be formulated into acceptable dosage forms by conventional methods known to those of skill in the art. For example, acceptable carriers include, but are not limited to, sugars (e.g., lactose, sucrose, mannitol, and sorbitol), silicon dioxide, starches, cellulose preparations (such as microcrystalline cellulose), calcium phosphates (e.g., dicalcium phosphate, tricalcium phosphate and calcium hydrogen phosphate), sodium citrate, water, aqueous solutions, alcohols (e.g., ethyl alcohol, propyl alcohol, and benzyl alcohol), polyols (e.g., glycerol, propylene glycol, and polyethylene glycol), organic esters (e.g., ethyl oleate and triglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes, paraffins, silicones, talc, salicylate, etc.

Each acceptable carrier used in a pharmaceutical composition or nutritional supplement of the invention must be "acceptable" in the sense of being compatible with the other ingredients of the formulation and not injurious to the subject. Carriers suitable for a selected dosage form and intended route of administration are well known in the art, and acceptable carriers for a chosen dosage form and method of administration can be determined using ordinary skill in the art.

As mentioned above, the Withanolide-enriched pharmaceutical compositions and nutritional supplements of the invention may, optionally, contain additional ingredients and/or materials commonly used in pharmaceutical compositions and/or nutritional supplements. Such ingredients and materials include (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxy methyl cellulose and sodium carbonate; (5) solution retarding agents, such as paraffin; (6) absorption accelerators, such as quaternary ammonium compounds; (7) wetting agents, such as cetyl alcohol and glycerol monosterate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monosterate, gelatin, and waxes; (18) opacifying agents; (19) adjuvants; (20) wetting agents; (21) emulsifying and suspending agents; (22), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; (28) vitamins and minerals; (29) proteins that carry therapeutic or nutritional benefits, such as whey protein and other milk-derived proteins; and (30) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

Pharmaceutical compositions and nutritional supplements suitable for oral administration may be in the form of capsules, cachets, pills, tablets, powders, granules, a solution or a suspension in an aqueous or non-aqueous liquid, an oil-in-water or water-in-oil liquid emulsion, an elixir or syrup, or a paste. These formulations may be prepared by methods known in the art, e.g., by means of conventional pan-coating, mixing, granulation or lyophilization processes.

Solid dosage forms for oral administration (capsules, tablets, pills, powders, granules and the like) may be prepared by mixing the active ingredient(s) with one or more acceptable carriers and, optionally, one or more fillers, extenders, binders, humectants, disintegrating agents, solution retarding agents, absorption accelerators, wetting agents, absorbents, lubricants, and/or coloring agents. Solid compositions of a similar type may be employed as fillers in soft and hard-filled gelatin capsules using a suitable excipient. A tablet may be made by compression or molding, optionally with one or more accessory ingredients. Compressed tablets may be prepared using a suitable binder, lubricant, inert diluent, preservative, disintegrant, surface-active or dispersing agent. Molded tablets may be made by molding in a suitable machine. The tablets, and other solid dosage forms, such as capsules, pills and granules, may optionally be scored or prepared with coatings and shells, such as enteric coatings and other coatings well known in the art. The tablets, and other solid dosage forms, may also be formulated so as to provide slow or controlled release of the active ingredient therein. They may be sterilized by, for example, filtration through a bacteria-retaining filter. These compositions may also optionally contain opacifying agents that release the active ingredient only, or preferentially, in a certain portion of the gastrointestinal tract, optionally, in a delayed manner. The active ingredient can also be in a microencapsulated form.

Liquid dosage forms for oral administration include acceptable emulsions, microemulsions, solutions, suspensions, syrups, and elixirs. The liquid dosage forms may contain suitable inert diluents commonly used in the art. Besides inert diluents, the oral compositions may also include adjuvants, such as wetting agents, emulsifying and suspending agents, sweetening, flavoring, coloring, perfuming and preservative agents. Suspensions may contain suspending agents.

According to yet further embodiments of the present invention, concentrated forms of Withanolides, along with methods of using such concentrated forms of Withanolides described herein, for induction of autophagy within hair follicle cells are provided. More particularly, as described above, such compositions will include elevated amounts of one or more of the Withanolides described herein, such that the final concentration of Withanolides is at least 10% (w/w), or at least 15% (w/w), or at least 20% (w/w), or at least 25% (w/w), or at least 30%, 40%, 50%, 60%, 70%, 80%, or 90% (w/w) of the Ashwagandha extract, with the balance optionally consisting essentially of (or consisting entirely of) natural extracts of Ashwagandha (*Withania somnifera*), including whole plant extracts, root extracts, leaf extracts, or a combination of such extracts—which, optionally, may then be combined with the oils, carriers, and inactive ingredients mentioned below. In certain preferred embodiments, as described above, the Withanolide-enriched Ashwagandha extract will include no less than 20% (w/w) or, in certain embodiments, no less than 25% (w/w) Withaferin A, relative to the total modified natural extract of Ashwagandha.

In these embodiments, the invention provides that such Withanolide-enriched Ashwagandha extract may be applied to a person's scalp or skin in general to modulate mTOR, TERT, and/or β-Catenin (as described above) and, moreover, to induce autophagy within such hair follicle cells. In addition, the present invention encompasses methods of using such Withanolide-enriched Ashwagandha extract and concentrated forms of Withanolides for (a) increasing and inducing the anagen growth phase of hair follicles; (b) reactivating dormant hair follicle cells to facilitate the growth and regeneration of such cells; and/or (c) to facilitate antioxidant status, improved biological age, and biological health of skin cells.

The invention provides that such concentrated forms of Withanolides are preferably formulated for topical scalp or more generally skin applications. In some embodiments, the Withanolide-enriched compositions may further include one or more essential oils, such as almond oil, cedarwood oil, chamomile oil, clary sage oil, coconut oil, and/or others. Still further, the Withanolide-enriched compositions may further include and be added to other acceptable carriers (inactive ingredients) for topical scalp applications, such as various alcohols, propylene glycol, water, and/or various surfactants (such as sodium lauryl sulfate, sodium laureth sulfate, cocamidopropyl betaine, and/or others).

EXAMPLES

The following Examples demonstrate, among other things, the efficacy of certain Withanolide-enriched Ashwagandha compositions of the present invention, which include an Ashwagandha root extract augmented with active Withanolide. Specifically, the Ashwagandha compositions of the present invention analyzed in Examples 1-7 consisted of Ashwagandha root extract, augmented with additional Withaferin A. More specifically, the Ashwagandha compositions of the present invention analyzed in Examples 1-7 consisted of Ashwagandha root extract, augmented with additional Withaferin A, having up to (but no more than) 1.5% (w/w) Withaferin A and not less than 10% (w/w) total Withanolides—as measured by gravimetric HPLC. Such Ashwagandha compositions of the present invention, as referenced in FIGS. 1-7, are referred to herein as "AshWITH." More particularly, the AshWITH composition tested in Examples 1-7 below was an Ashwagandha natural root extract supplemented with additional Withaferin A, which included approximately 1%-1.5% (w/w) Withaferin A, and approximately 10%-15% (w/w) total Withanolides. The efficacy of the AshWITH compositions were tested and compared to generic and brand versions of Ashwagandha extracts.

Example 1: Antioxidant Activity of AshWITH

Antioxidant activity of various Ashwagandha samples was measured using a 2,2-diphenyl-1-picrylhydrazyl (DPPH) radical scavenging assay. DPPH is a stable free radical that produces violet solution in ethanol and, upon reduction by antioxidant compounds, produces light yellow-to-colorless solutions.

For comparative antioxidant activity analysis of AshWITH, relative to non-branded and branded Ashwagandha compositions, two different dilutions (100 μg/ml and 1000 μg/ml) of each sample were prepared in ethanol and 500 μl of each sample dilution was mixed (1:1) with 500 μl of 0.04 mg/ml DPPH (Sigma #D9132-1G) ethanolic solution. Gallic acid (a natural polyphenolic antioxidant) and sucrose were used as positive and negative controls, respectively. All samples and controls were thoroughly vortexed and incubated for 30 minutes at room temperature in the dark followed by absorbance (Abs) readings at 517 nm using a spectrophotometer. Percentage antioxidant activity was calculated using the formula: 100−(AbsSample−AbsBlank/AbsControl×100), where AbsSample=Sample Dilution+DPPH Solution; AbsBlank=Sample Dilution+DPPH solvent; and AbsControl=Sample Solvent+DPPH Solution.

In this Example, and as illustrated in FIG. 1, the AshWITH composition of the present invention exhibited significantly higher antioxidant activity when compared to non-branded and branded Ashwagandha extracts. More particularly, the AshWITH composition showed strong and significantly higher anti-oxidant potential, with the percent anti-oxidant activity ("% AA") at 100 μg/ml measured at 45.13±3.16 and the % AA at 1000 μg/ml was 90.26±1.43%, when compared with the branded Ashwagandha extract at both the 100 μg/ml and 1000 μg/ml dilutions (% AA at 100 μg/ml was 12.24±4.63 and % AA at 1000 μg/ml was 22.55±5.45) ($P=0.0006$ and $P<0.0001$, respectively) (FIG. 1). At a higher dilution (1000 μg/ml), the AshWITH composition and Gallic acid were found to have similar % AA (% AA of AshWITH was 90.26±1.43% and % AA of Gallic acid was 90.12±1.1).

Example 2: Cytotoxicity of AshWITH

Figure 2:
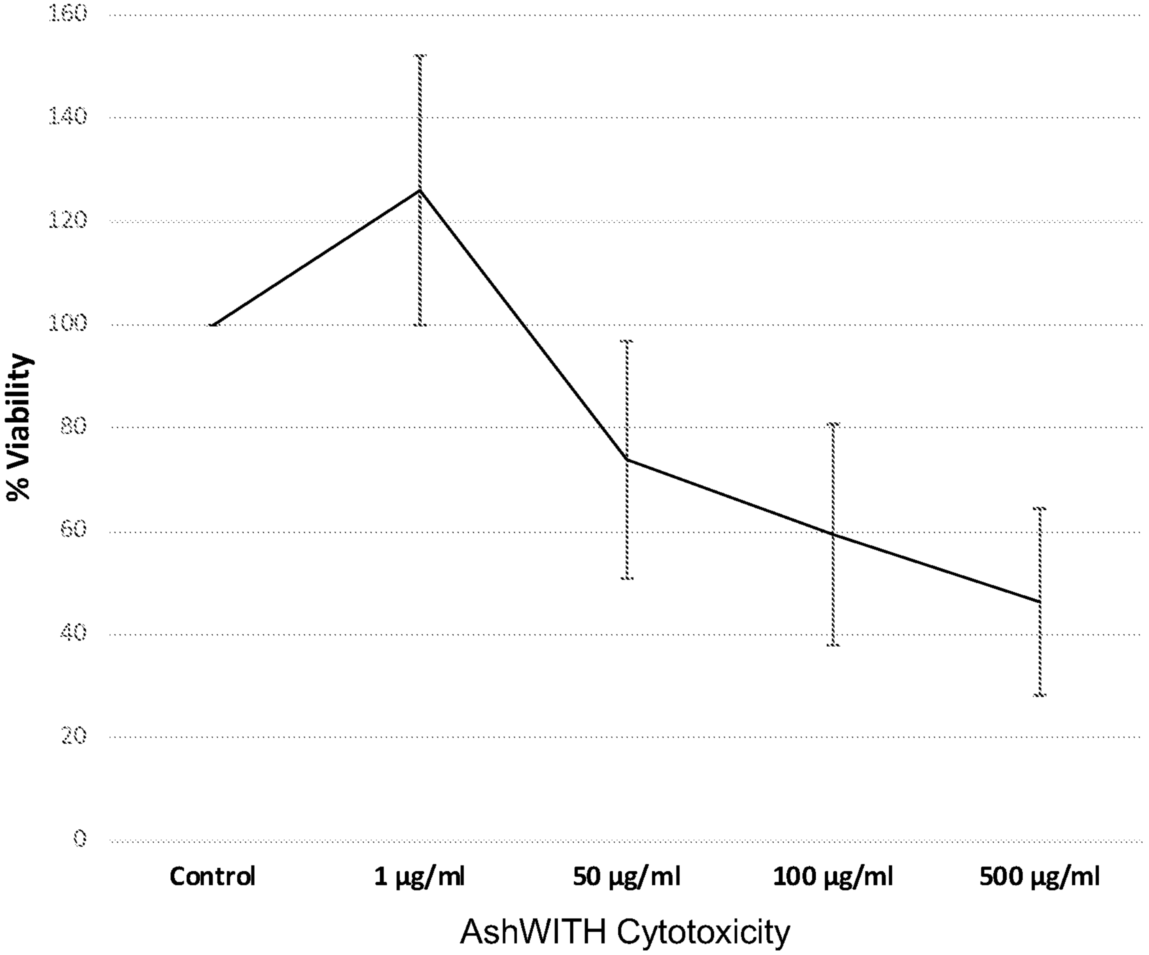
FIG. 2 is a line graph that summarizes the cytotoxic effects of the Ashwagandha/Withanolide-enriched compositions of the present invention (from low to higher concentrations).
Figure 3:
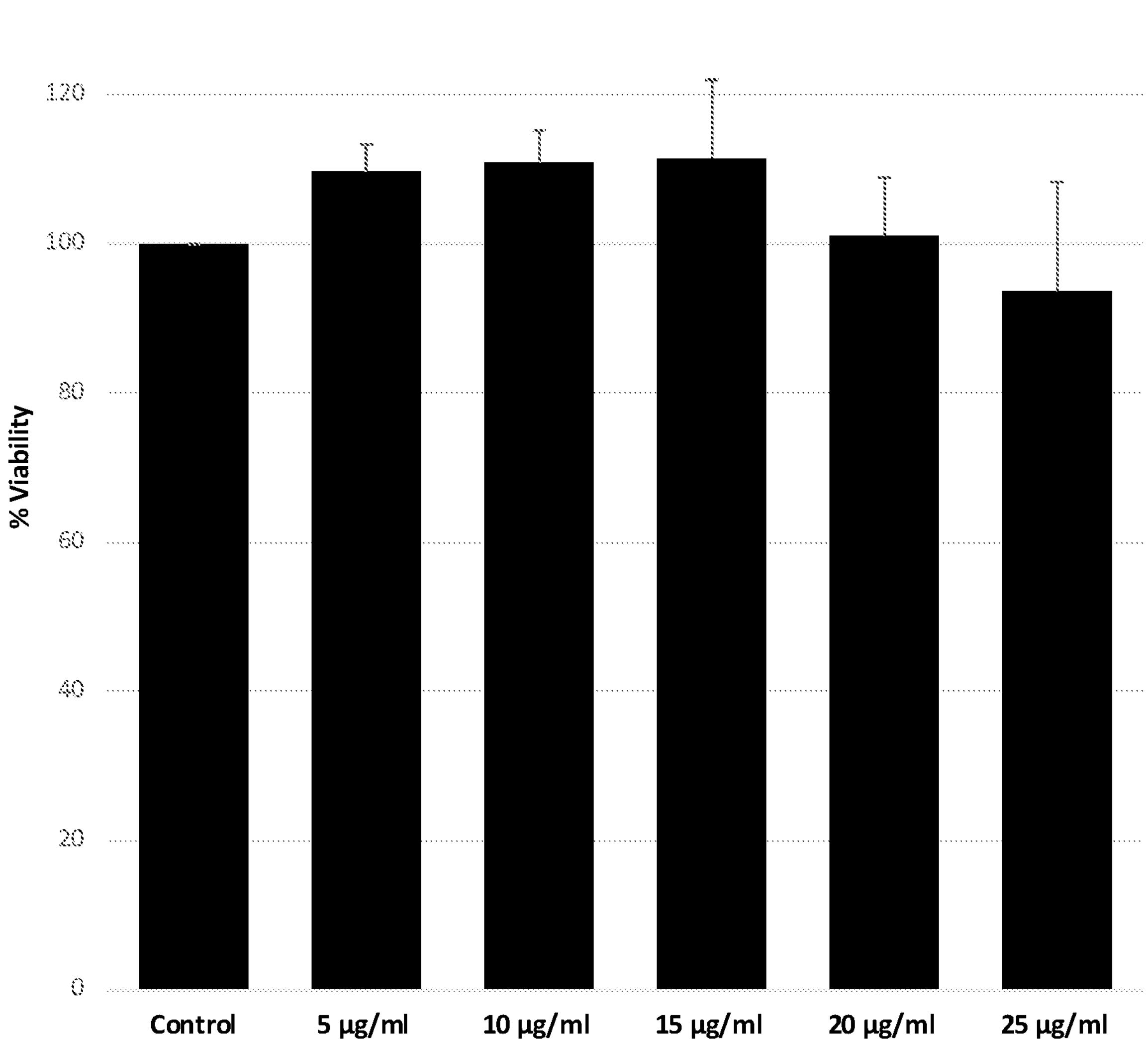
FIG. 3 is a bar graph that summarizes the cytotoxic effects of the Ashwagandha/Withanolide-enriched compositions of the present invention (at lower concentrations).

In this Example, 3-(4,5-Dimethylthiazol-2-yl)-2,5-Diphenyltetrazolium Bromide (MTT) cell viability assays were performed to measure the cytotoxic effects of AshWITH on HEK293 cells. A 1 mg/ml primary stock solution of AshWITH was prepared in 1% DMSO in PBS for the cell treatments described in this Example. The HEK293 cells were initially treated at a higher concentration range (1, 50, 100 and 500 μg/ml) for 24 hours—and the percent cell viability was subsequently measured with reference to the control. The survival rate of cells treated with AshWITH at 50 μg/ml was approximately 73% and at 100 μg/ml was approximately 59% (P=0.0305) (FIG. 2). To determine non-cytotoxic doses of AshWITH for subsequent mechanistic studies, cells were treated at a lower concentration range (5, 10, 15, 20 and 25 μg/ml) for 24 hours and cell viability was subsequently measured. The results showed no significant alteration in percentage of surviving cells treated at such lower concentration ranges when compared with control cells (FIG. 3). Moreover, 5-15 μg/ml doses were shown to have positive effects on cell survival and cellular proliferation. Hence, in the experiments described below in Examples 3-7, the AshWITH compositions tested were 15 μg/ml or lower.

Example 3: Cytoprotection Efficacy of AshWITH

It is known that free radicals and reactive oxygen species (ROS) are natural by-products of aerobic respiration in living organisms, which are crucial for many cellular signaling pathways. However, accumulation of ROS due to imbalances between production and removal—a condition often referred to as oxidative stress—is detrimental to cells and tissues and eventually leads to initiation and progression of various pathological conditions, such as pre-mature aging, atherosclerosis, vascular diseases, diabetes, cancer, and others. To counter such effects, humans are equipped with anti-oxidant defense machinery that includes various antioxidant enzymes and molecules. However, in today's world, humans are constantly exposed to environmental pollutants, ultraviolet radiation, and harmful chemicals, as well as experience-induced stress and anxiety in various forms, which lead to redox imbalance and accumulation of free radicals. Compositions that exhibit antioxidant properties can be used as free radical scavengers to mitigate such oxidative stresses.

Figure 4:
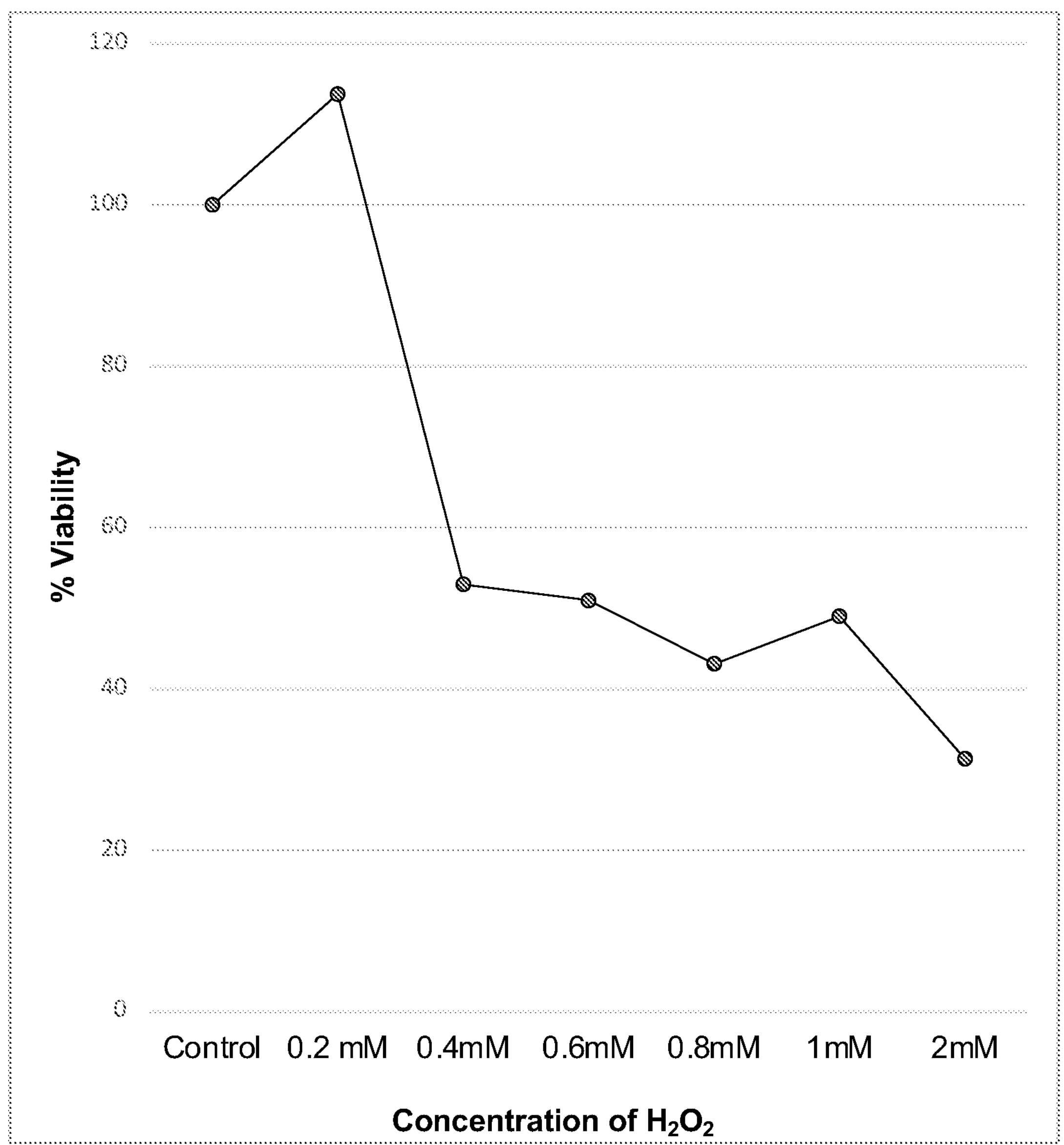
FIG. 4 is a line graph that summarizes hydrogen peroxide ($H_2O_2$) dose optimization for oxidative stress induction in HEK293 cells.

In this Example, 3-(4,5-Dimethylthiazol-2-yl)-2,5-Diphenyltetrazolium Bromide (MTT) cell viability assays were performed to compare cytoprotection efficacy of various Ashwagandha samples against oxidative stress induced cellular damage. More particularly, hydrogen peroxide ($H_2O_2$) was used to induce oxidative stress in cultured HEK293 (Human Embryonic Kidney) cells at various molar concentrations, namely, 0.2, 0.4, 0.6, 0.8, 1, and 2 mM. Cell viability was analyzed using the MTT assay described herein. Decreases in cell viability with increasing doses of $H_2O_2$ was observed and, at 0.4 mM, cell survival rate was approximately 50%. Therefore, a 0.4 mM $H_2O_2$ dose was considered as $IC_{50}$ for $H_2O_2$ treatment in this Example for oxidative stress induction in HEK293 cells (FIG. 4).

In addition, in this Example, $10\times10^3$ HEK293 cells were seeded per well of a 96-well plate in 100 μl DMEM and 10% Fetal Bovine Serum (FBS) media. Cells were allowed to adhere overnight followed by treatment as follows: (1) Control (DMSO); (2) $H_2O_2$ only (0.4 mM); (3) $H_2O_2$ (0.4 mM) along with 15 μg/ml of AshWITH; (4) $H_2O_2$ (0.4 mM) along with 15 μg/ml of non-branded Ashwagandha ("Ash"); and (5) $H_2O_2$ (0.4 mM) along with branded Ashwagandha (15 μg/ml) for 24 hours.

The percentage of cell viability was calculated using an MTT assay according to standard protocols. More particularly, after completion of incubation, treatment media was removed from the respective wells and 100 μl of fresh media, along with 10 μl of 5 mg/ml MTT (Sigma-Aldrich) solution, were added to all wells, including the control wells and the blank wells. After 3 hours of incubation at 37° C., media containing MTT was removed and 80 μl DMSO was added per well to dissolve formazan crystals. Absorbance of the formazan crystals dissolved in DMSO was subsequently measured at 540 nm using a SpectraMax i3X plate reader. The percentage cell viability was calculated as follows: [(AbsSample−AbsBlank/AbsControl−AbsBlank)×100]. The percent cell viability was measured with reference to the control wells.

Figure 5:
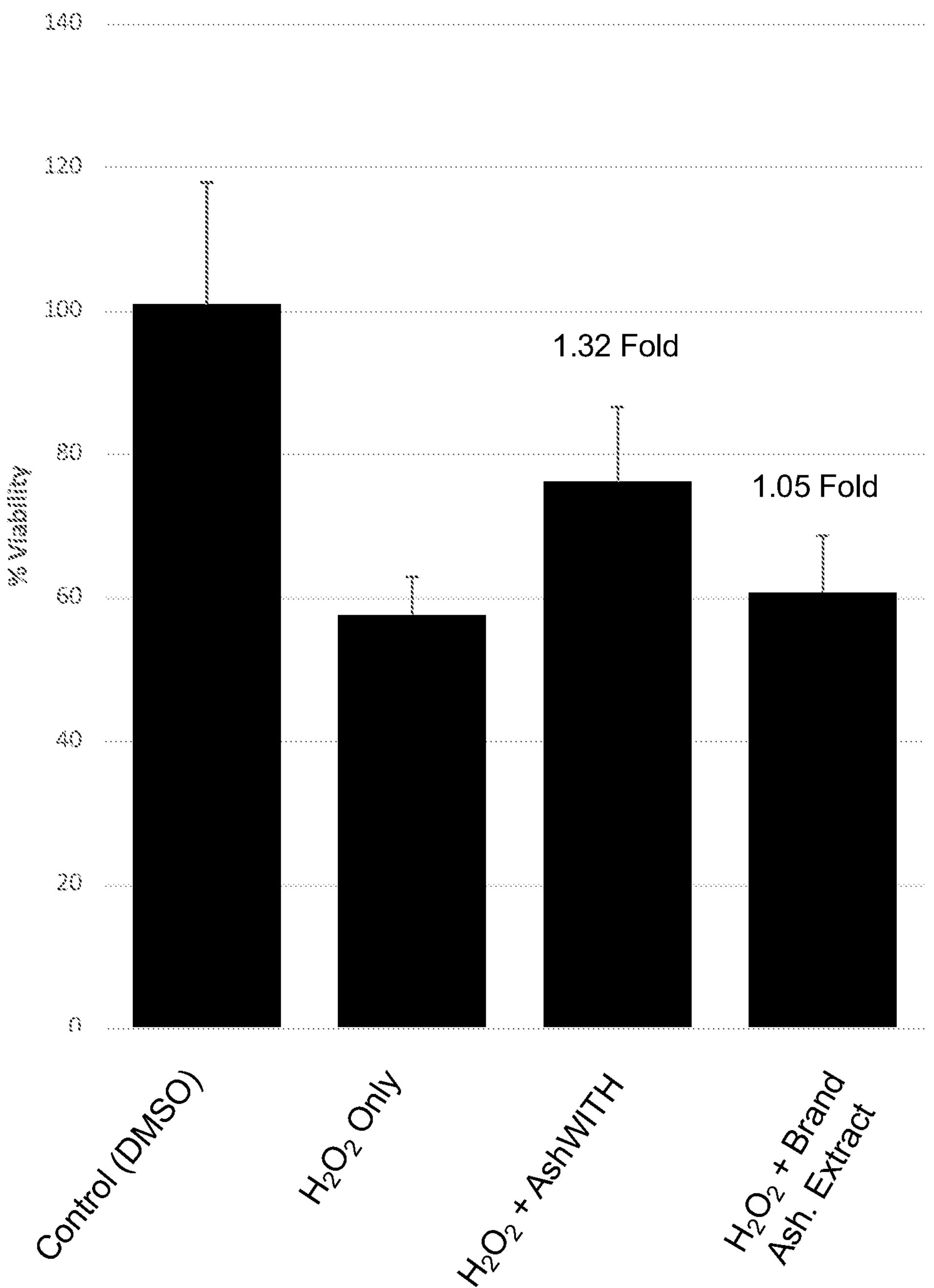
FIG. 5 is a bar graph that summarizes cytoprotection efficacy comparisons of brand Ashwagandha extracts and the Ashwagandha/Withanolide-enriched compositions of the present invention against oxidative stress induced cell death.
Figure 6:
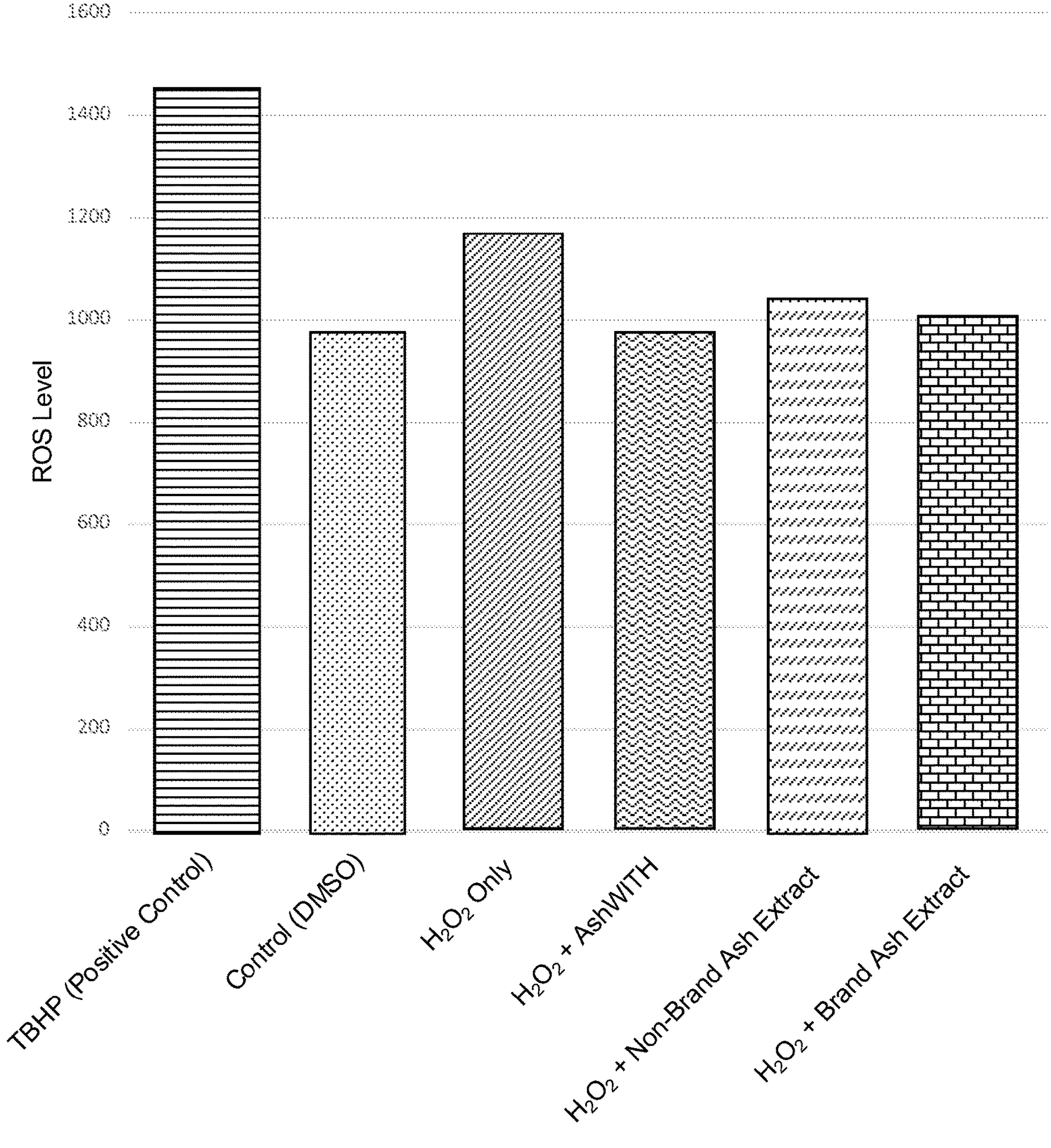
FIG. 6 is a bar graph that summarizes ROS levels in cells treated with generic (non-brand) Ashwagandha extracts; brand Ashwagandha extracts; and the Ashwagandha/Withanolide-enriched compositions of the present invention, which have also been exposed to hydrogen peroxide ($H_2O_2$).
Figure 7:
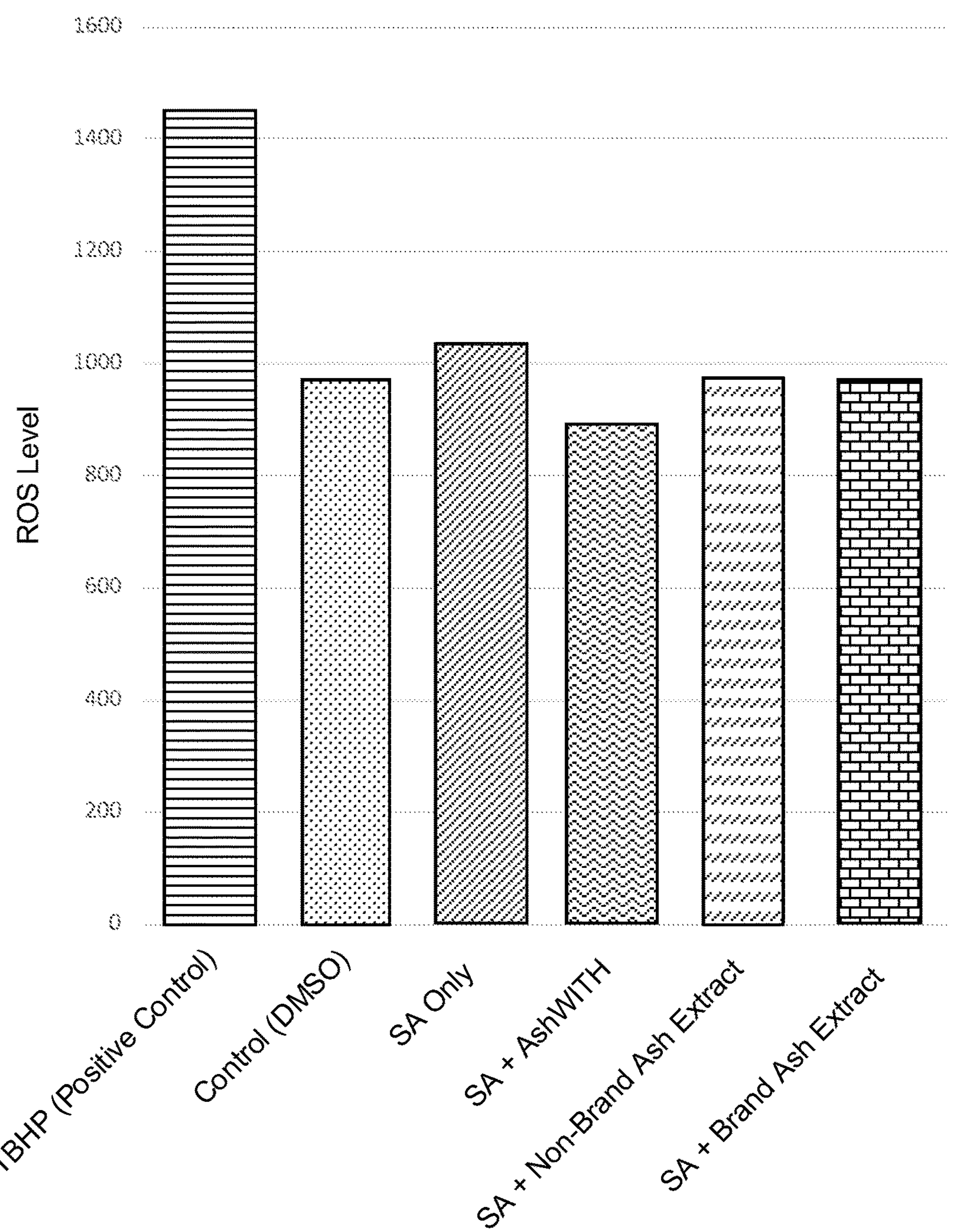
FIG. 7 is a bar graph that summarizes ROS levels in cells treated with generic (non-brand) Ashwagandha extracts; brand Ashwagandha extracts; and the Ashwagandha/Withanolide-enriched compositions of the present invention, which have also been exposed to sodium arsenite (SA).

As summarized in FIG. 5, $H_2O_2$-treated HEK293 cells exhibited severe decline in cell survival as compared to untreated control cells. As further summarized in FIG. 5, the results showed 57.68±5.30% cell survival in $H_2O_2$ only treated cells; whereas, 76.28±10.38% cell survival (1.32 fold higher than $H_2O_2$ only group) was observed in AshWITH+$H_2O_2$ treated cells and 60.79±7.90% cell survival (1.05 fold higher than $H_2O_2$ only group) in branded Ashwagandha+$H_2O_2$ treated cells. The difference in cell survival rate between $H_2O_2$ only and $H_2O_2$+AshWITH treatment groups was statistically significant (P=0.0186), which indicates higher potential of AshWITH to protect cells when injured by oxidative stress.

Example 4: Reactive Oxygen Species (ROS) Levels

In this Example, reactive oxygen species (ROS) lowering potentials of different Ashwagandha samples were compared using a 2',7'-dichlorofluorescin diacetate (DCFDA) cellular ROS assay kit (Abcam ab113851). Hydrogen peroxide ($H_2O_2$) and sodium arsenite (SA) were used to induce oxidative stress by increasing cellular ROS in HEK293 cells. TBHP (tert-Butyl hydroperoxide) was used as a positive control for ROS generation.

In this Example, the cells treated with the AshWITH composition of the present invention showed higher potential to reduce intracellular ROS level caused by both $H_2O_2$ (FIG. 6) and sodium arsenite (SA) (FIG. 7), compared to non-branded and branded Ashwagandha co-treated cells, suggesting enhanced free radical scavenging capacity of AshWITH.

Example 5: Expression of Intracellular Glutathione Peroxidase

Glutathione Peroxidase (also referred to herein as GPx and GPX1) is a major intracellular antioxidant enzyme whose main biological function is to protect an organism from oxidative damage. GPx was first identified in 1957 as an enzyme that protects red blood cells against hydrogen peroxide ($H_2O_2$). GPx catalyzes the conversion of $H_2O_2$ to $H_2O$ and $O_2$ via oxidation of reduced GSH into its disulfide form (GSSG).

In this Example, intracellular GPX1 levels were compared in oxidative stress induced HEK293 cells co-treated with different Ashwagandha samples using a semi-quantitative dot blot method. More specifically, 10,000 HEK293 cells were seeded per well of 6-well plates and cultured until the cells were 60-70% confluent. Next, the cells were treated as follows: (1) Control (DMSO); (2) $H_2O_2$ (0.4 mM) only; (3) $H_2O_2$ along with the AshWITH composition of the present invention (15 μg/ml); (4) $H_2O_2$ along with non-branded Ashwagandha (15 μg/ml); and (5) $H_2O_2$ along with branded Ashwagandha (15 μg/ml) for 22 hours. Cells were harvested, total protein was quantified, and 2 μg of protein per sample was spotted onto a nitrocellulose membrane and probed with an anti-GPX1 antibody (Abcam #ab22604). Dot blot membranes were imaged using a BioRad Fluor-S Max multi-Imager, with spot intensity quantified using Quantity one software.

Figure 8:
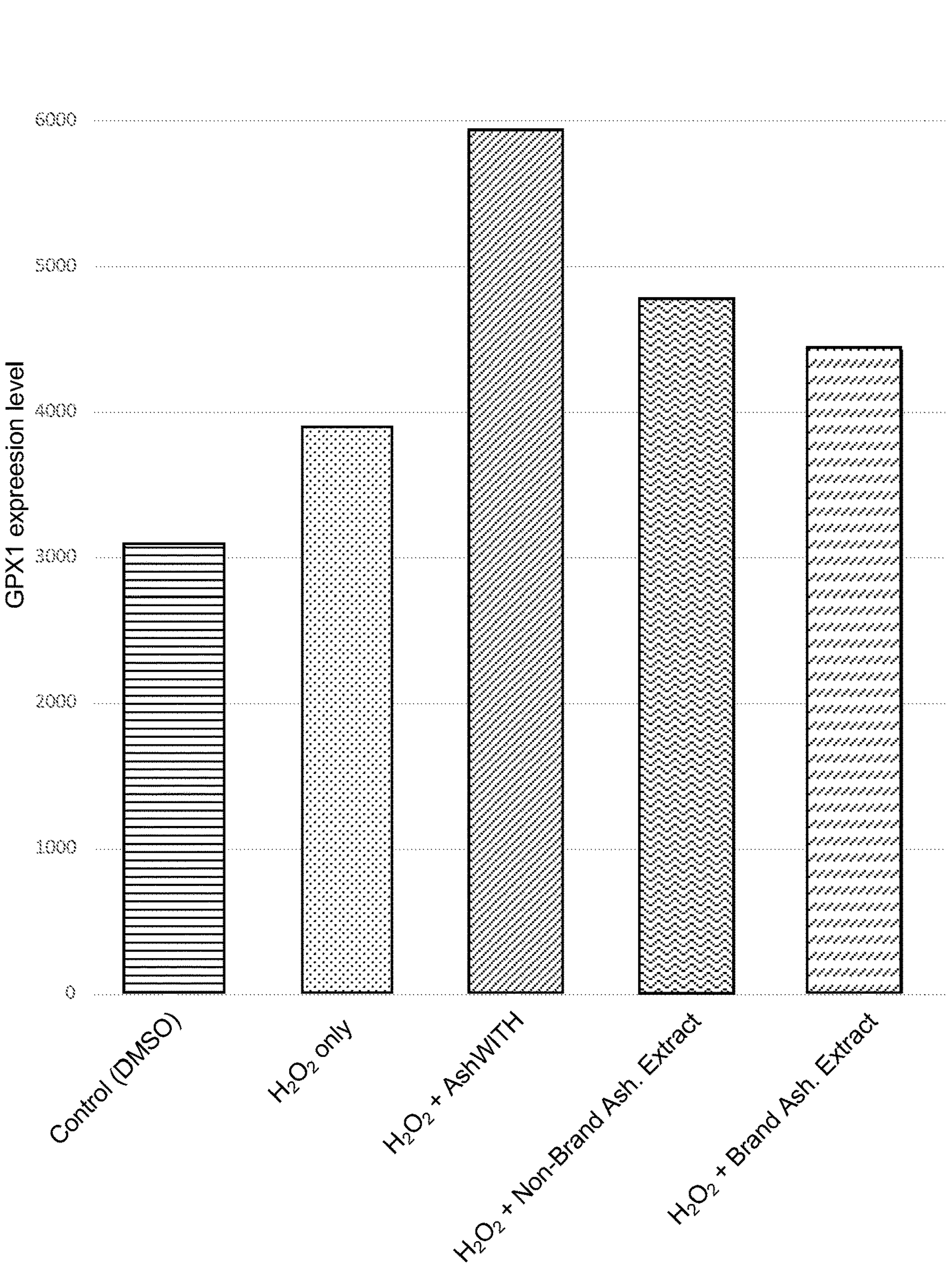
FIG. 8 is a bar graph that summarizes glutathione peroxidase (GPX1) expression observed in HEK293 cells treated with generic Ashwagandha extracts; brand Ashwagandha extracts; and the Ashwagandha/Withanolide-enriched compositions of the present invention.

As shown in FIG. 8, Ashwagandha co-treated cells showed upregulation in GPX1 expression compared to the $H_2O_2$-only group, with the highest GPX1 expression observed in cells with the AshWITH composition (compared to non-branded and branded Ashwagandha co-treated cells). In addition, as shown in Examples 1-5 above, the AshWITH composition of the present invention showed significantly higher antioxidant activity over other Ashwagandha extracts tested. Still further, such AshWITH composition showed enhanced cytoprotection efficacy, thereby providing cells and tissues an enhanced capacity to resist stress and workload.

Example 6: AshWITH Modulates Cellular Nrf2 Expression Levels

Figure 9:
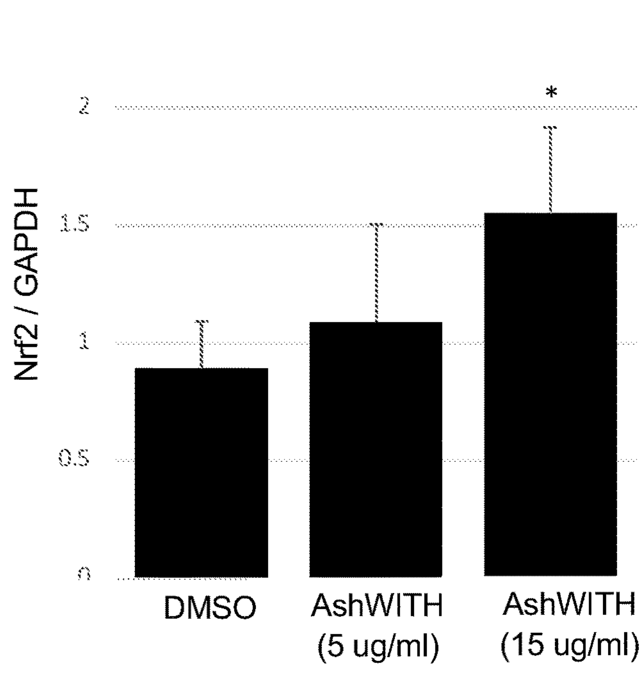
FIG. 9 is a bar graph that summarizes the Western blot results described in Example 6, showing the effects of AshWITH on Nrf2 expression levels (normalized by a GAPDH loading control) in resting HEK293 cells.
Figure 10:
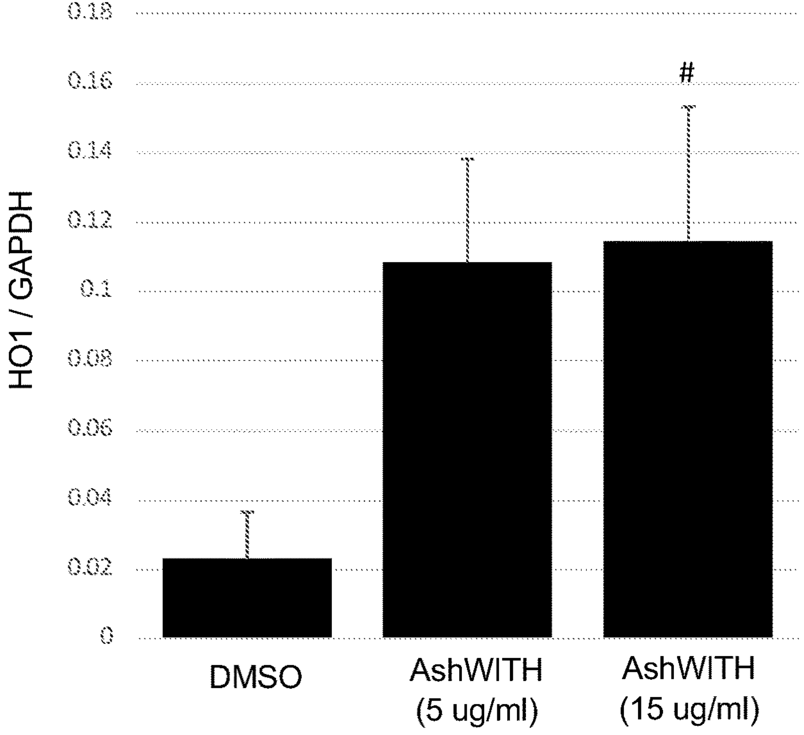
FIG. 10 is a bar graph that summarizes the Western blot results described in Example 6, showing the effects of AshWITH on HO1 expression levels (normalized by a GAPDH loading control) in resting HEK293 cells.
Figure 11:
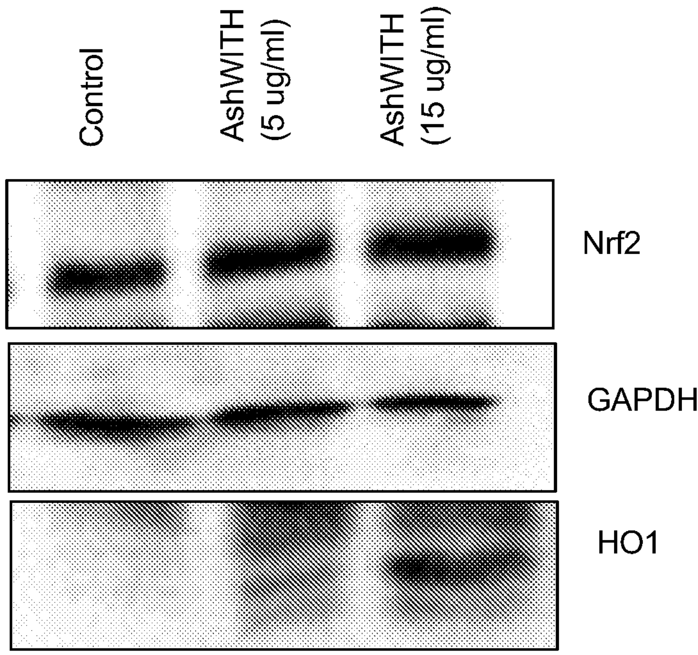
FIG. 11 are images of representative Western blots for Nrf2 and HO1 expression in resting HEK293 cells.
Figure 12:
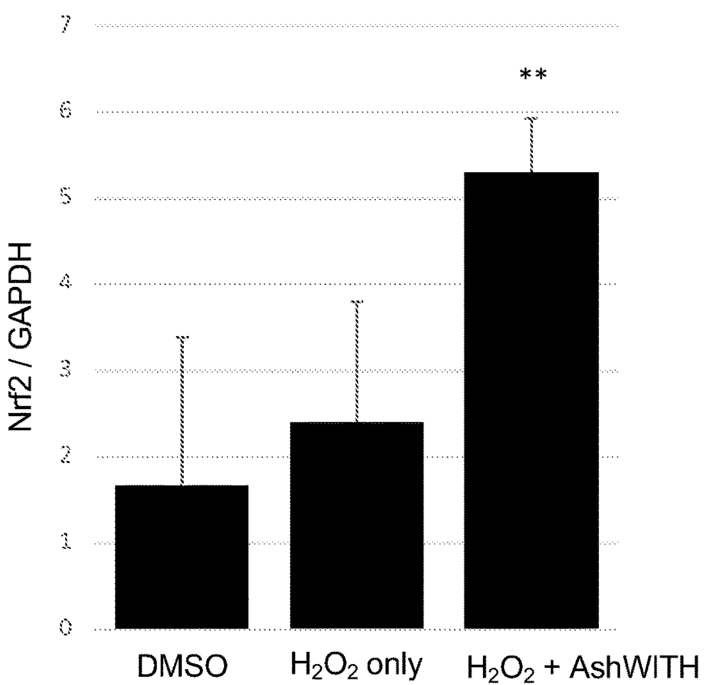
FIG. 12 is a bar graph that summarizes the Western blot results described in Example 6, showing the effects of AshWITH on Nrf2 expression levels (normalized by a GAPDH loading control) in $H_2O_2$ stressed HEK293 cells.
Figure 13:
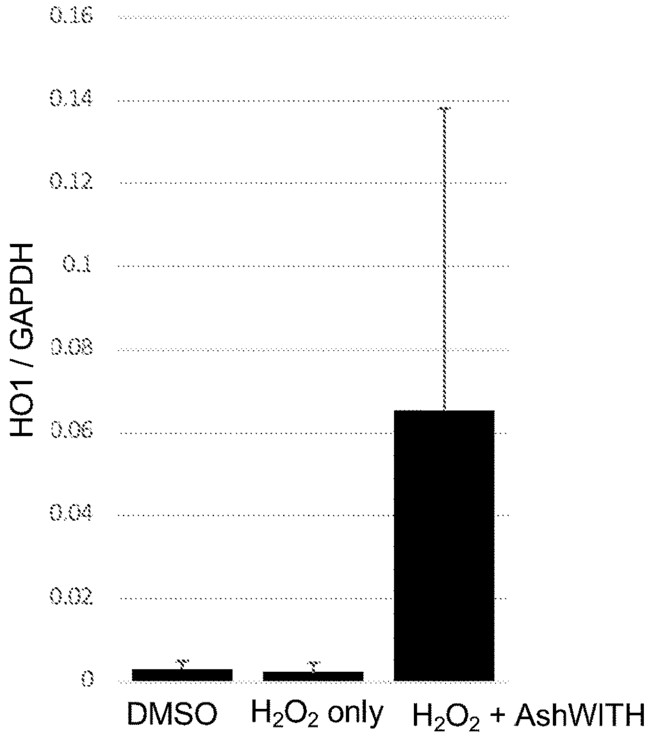
FIG. 13 is a bar graph that summarizes the Western blot results described in Example 6, showing the effects of AshWITH on HO1 expression levels (normalized by a GAPDH loading control) in $H_2O_2$ stressed HEK293 cells.
Figure 14:
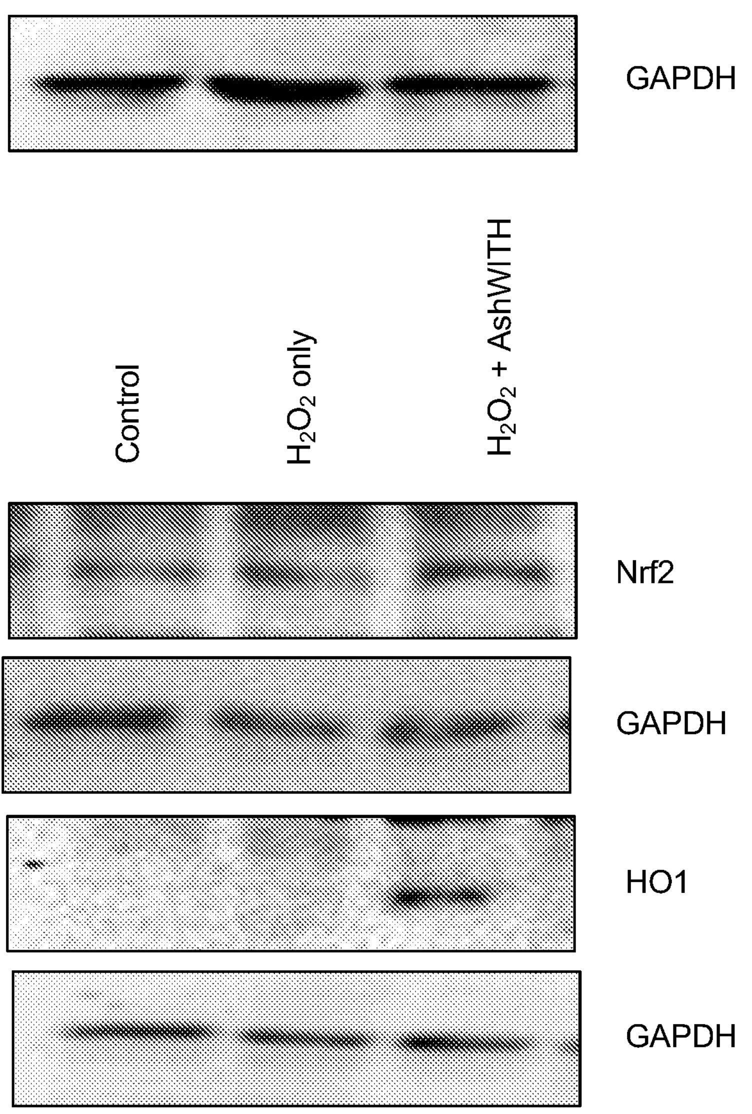
FIG. 14 are images of representative Western blots for Nrf2 and HO1 expression in $H_2O_2$ stressed HEK293 cells.

Nuclear factor erythroid 2-related factor 2 (Nrf2) is a major cytoprotective transcription factor that regulates expression of antioxidant enzymes by binding to antioxidant response elements under cellular stress. In this Example, Nrf2 and Heme oxygenase 1 (HO1, the downstream target of Nrf2 and phase II detoxifying enzyme) expression levels were measured by Western blotting after AshWITH treatment in resting and oxidative stress induced HEK293 cells. As shown in FIGS. 9-11, AshWITH treatment applied at 5 μg/ml and 15 μg/ml in resting HEK293 cells showed elevation in both Nrf2 and HO1 expression levels, compared to control cells (*P=0.05, #P=0.0076) (FIGS. 9-11).

In order to determine Nrf2 and HO1 modulation efficacy of AshWITH under oxidative stressed conditions, HEK 293 cells were treated with 15 μg/ml AshWITH in the presence and absence of $H_2O_2$ (0.4 mM) for 24 hours. AshWITH+$H_2O_2$ treated cells showed elevation in Nrf2 and HO1 expression, compared to the $H_2O_2$ only treatment group (**P=0.0212) (Figured 12-14).

Figure 15:
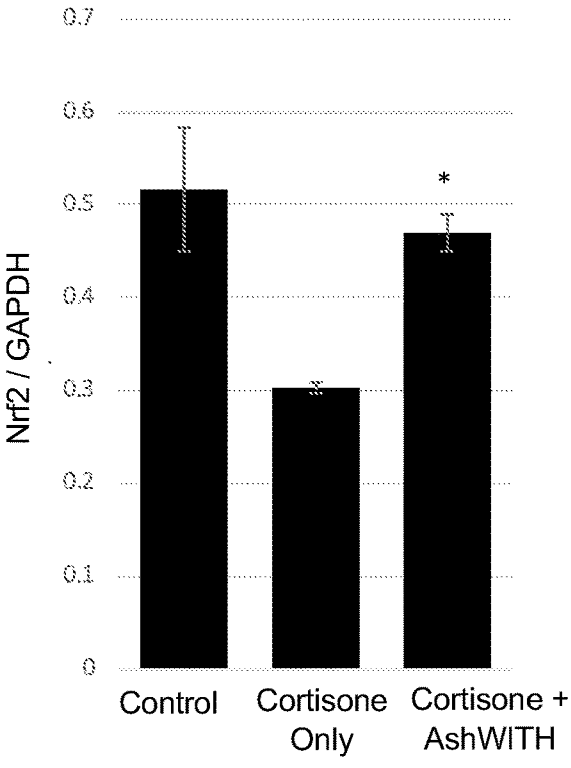
FIG. 15 is a bar graph that summarizes the Western blot results described in Example 7, showing the effects of AshWITH on Nrf2 expression levels (normalized by a GAPDH loading control) in cortisone stressed HEK293 cells.
Figure 16:
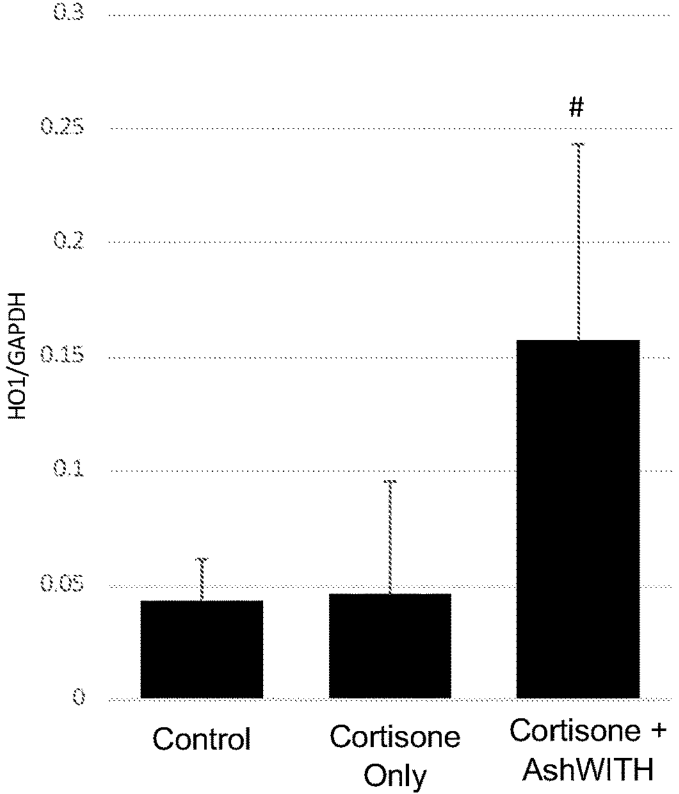
FIG. 16 is a bar graph that summarizes the Western blot results described in Example 7, showing the effects of AshWITH on HO1 expression levels (normalized by a GAPDH loading control) in cortisone stressed HEK293 cells.
Figure 17:
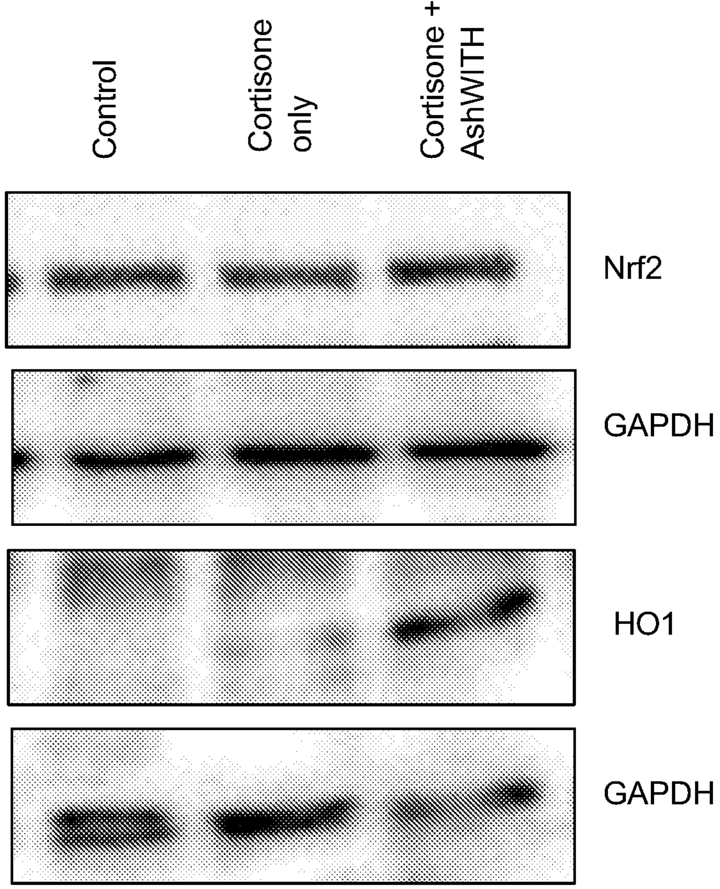
FIG. 17 are images of representative Western blots for Nrf2 and HO1 expression in cortisone stressed HEK293 cells.
Figure 18:
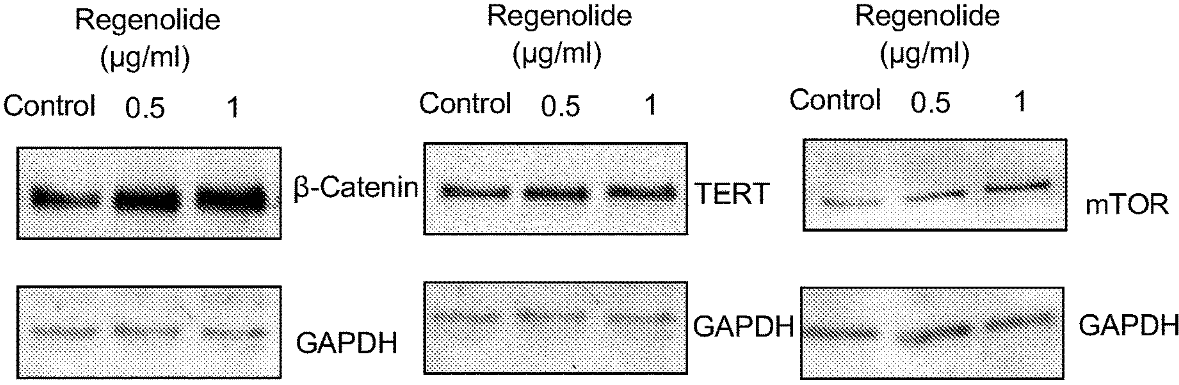
FIG. 18 includes Western blot results showing the effects of the Ashwagandha/Withanolide-enriched compositions of the present invention (Regenolide) on β-Catenin, TERT, and mTOR expression.
Figure 19:
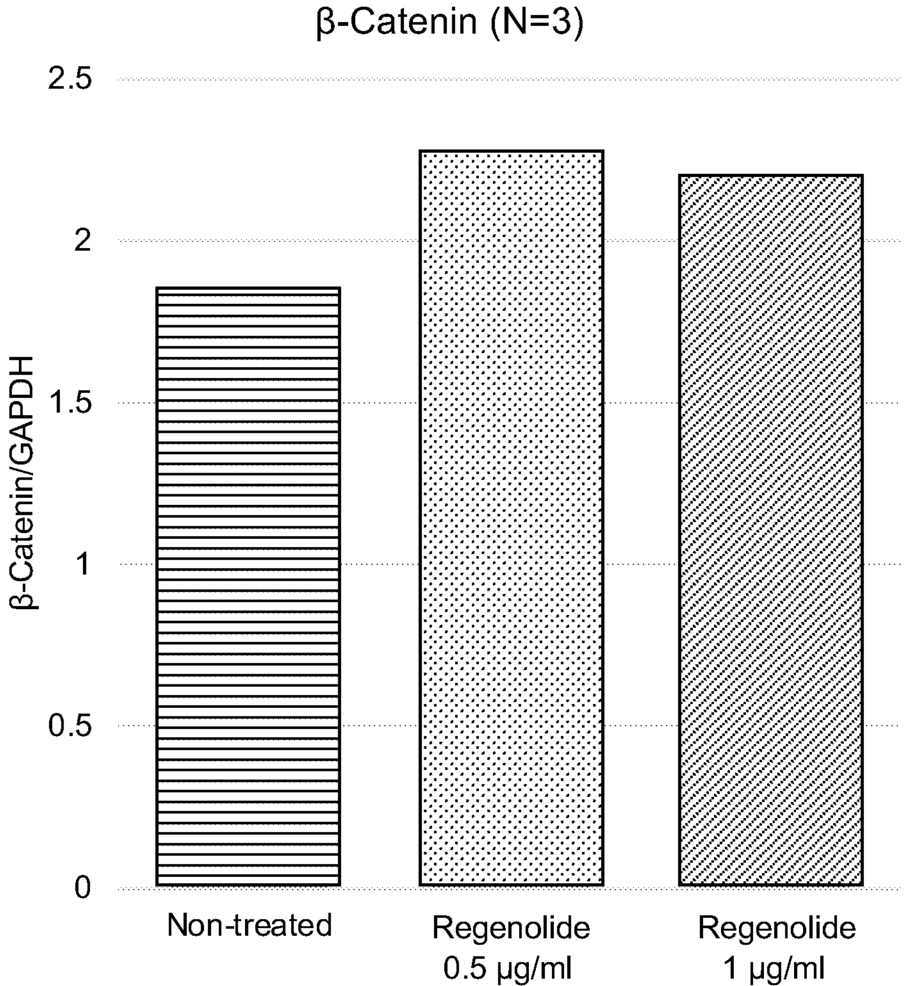
FIG. 19 is a bar graph showing the effects of the Ashwagandha/Withanolide-enriched compositions of the present invention (Regenolide) (at 0.5 μg/ml and 1 μg/ml for 24 hours) on β-Catenin expression in HFDPC cells.
Figure 20:
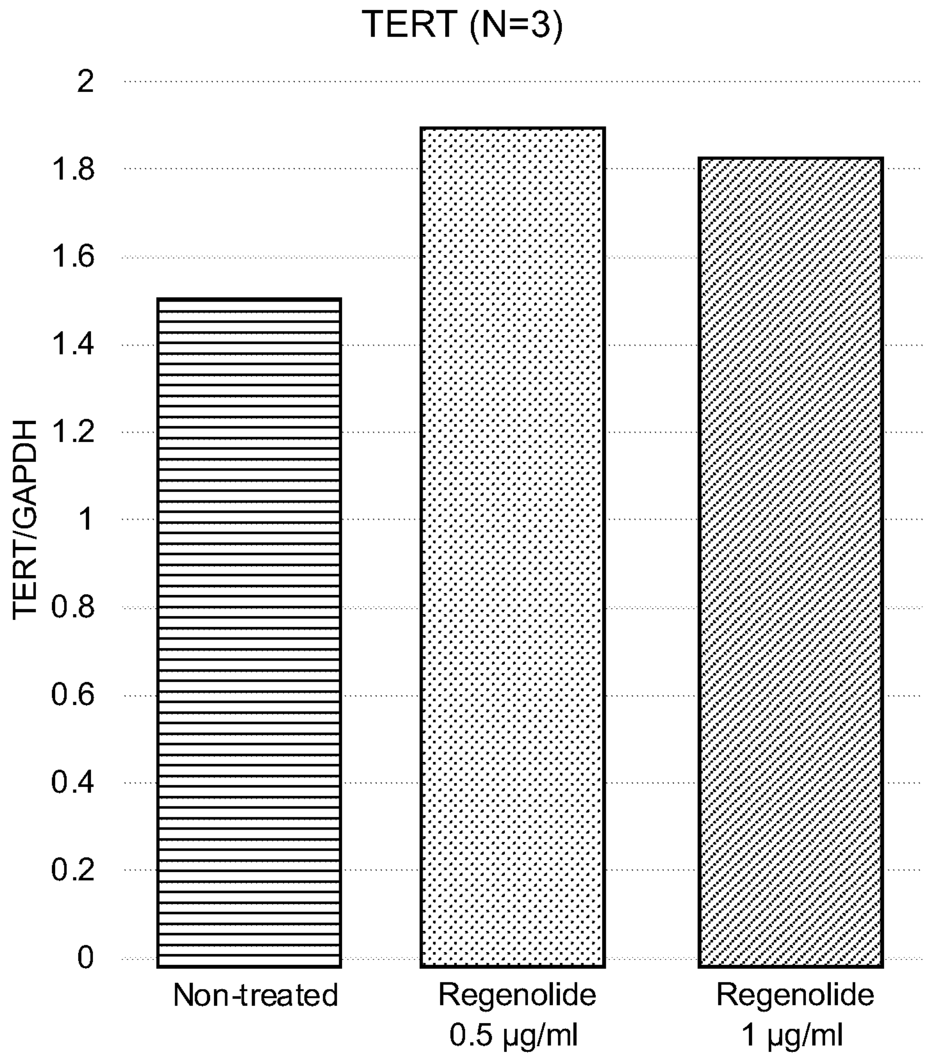
FIG. 20 is a bar graph showing the effects of the Ashwagandha/Withanolide-enriched compositions of the present invention (Regenolide) (at 0.5 μg/ml and 1 μg/ml for 24 hours) on TERT expression in HFDPC cells.
Figure 21:
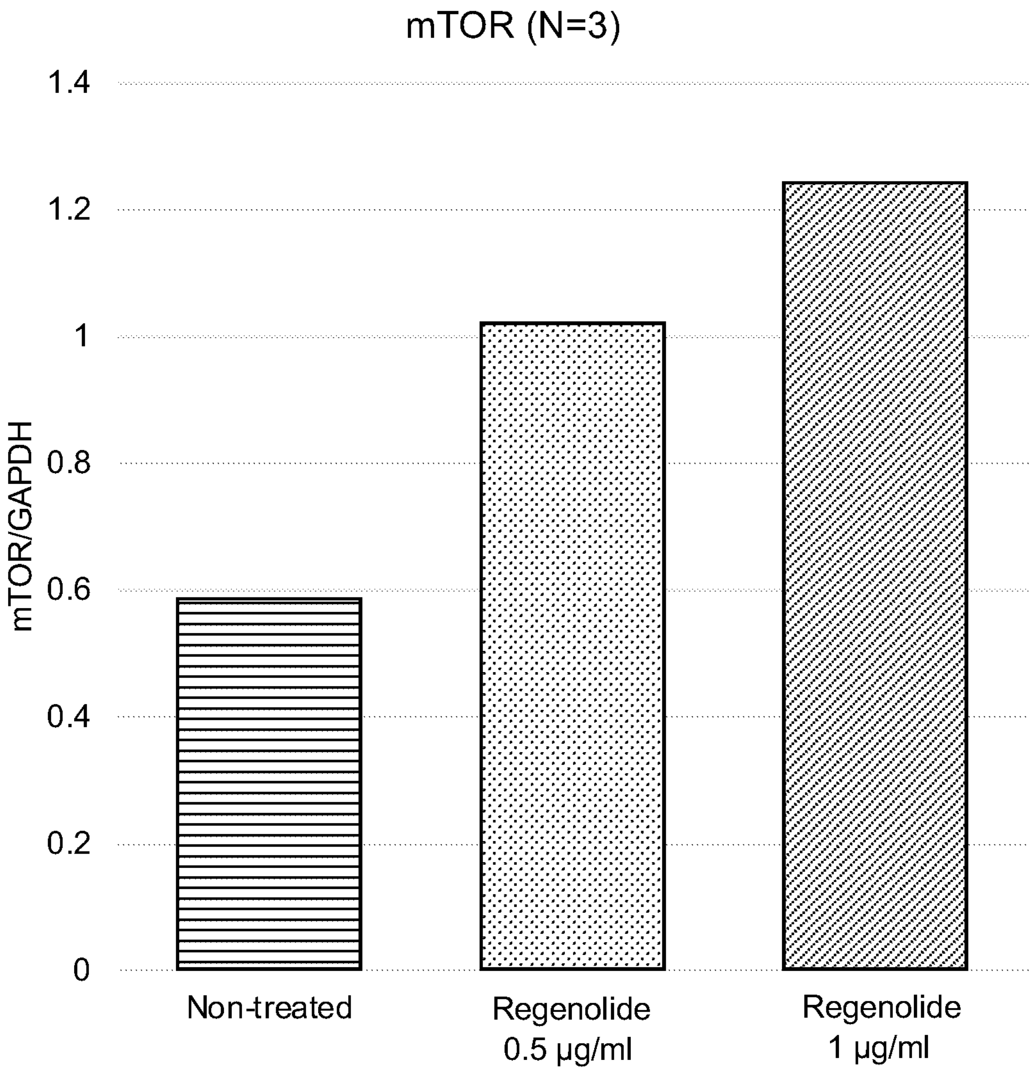
FIG. 21 is a bar graph showing the effects of the Ashwagandha/Withanolide-enriched compositions of the present invention (Regenolide) (at 0.5 μg/ml and 1 μg/ml for 24 hours) on mTOR expression in HFDPC cells.

Example 7: Upregulation of Nrf2/HO1 Signaling Axis in HEK293 Cells Stressed with Hydrocortisone In this Example, Nrf2 and HO1 expression levels were compared in HEK293 cells challenged with hydrocortisone (cortisone), in the presence and absence of AshWITH, via Western blot analysis. Such measurements provided further insight into the efficacy of AshWITH with regards to antioxidant signaling activation. More particularly, HEK294 cells were treated with (1) 1 mM cortisone or (2) cortisone (1 mM) and AshWITH (15 μg/ml) for 24 hours. As shown in FIGS. 15-18, the AshWITH co-treated cells showed significant increase in Nrf2 expression level, compared to cortisone only treated cells (*P=0.0001). Likewise, significant elevation in HO1 expression level was also observed in AshWITH and cortisone co-treated cells, in comparison to cortisone only treated cells (#P=0.0491) (FIG. 15-17).

Example 8: Regenolide Enhances Expression of Hair Growth Stimulating Factors in Human Hair Follicle Dermal Papilla Cells Hair is a protein filament that is primarily composed of alpha keratin and grows from hair follicles located in the dermal layer of the mammalian skin. Dermal papilla cells are mesenchymal cells that are present in the hair bulb located at the bottom of each hair follicle. These cells play a pivotal role in the development of hair follicles, keratinocytes activity, hair formation, and hair regrowth and cycle. To this end, the following Example demonstrates the hair growth instigating potential of the Regenolide compositions described herein.

In this Example, the Withanolide-enriched Ashwagandha extract composition included a Ashwagandha root extract, augmented with additional Withanolides, having no less than 25% (w/w) Withaferin A and not less than 30% (w/w) or, in some embodiments, not less than 35% (w/w) total Withanolides (referred to in this in Example 8 as "Regenolide"). More particularly, the Regenolide composition referenced in this Example was an Ashwagandha natural root extract supplemented with additional Withaferin A, which included approximately 25%-30% (w/w) Withaferin A and approximately 30%-40% (w/w) total Withanolides. In this Example, a 4 mg/ml Regenolide stock solution was prepared by dissolving 0.004 g of Regenolide in 1 ml of 20% DMSO in PBS solvent. This stock solution was sonicated for 20 seconds and vortexed at 10,000 rpm for 5 minutes.

The hair growth stimulating efficacy of the Regenolide composition was studied using primary human hair follicle dermal papilla cell culture (HFDPC, adult; Cell Application, Sigma-Aldrich #602-05A). Passage 2 frozen HFDPC cells were thawed and cultured on a TC-treated 100 mm tissue culture dish with HFDPC complete growth media (Sigma-Aldrich; 611-500). The media was replenished every 2 to 3 days until the cells were 80% confluent.

Next, 80% confluent HFDPC cells were trypsinized and approximately 5,000 cells/well were seeded in 6-well tissue culture plates in 2 ml HFDPC complete growth media. The cells were allowed to grow until they were 60-70% confluent. On the day of treatment, previous media was discarded and fresh media containing the Regenolide composition described above was added to each treatment well (A) at two different concentrations of 0.5 μg/ml and 1 μg/ml for 24 hours of incubation and (B) at 1 μg/ml concentration for 24 hours and 48 hours of incubation. Control cells were treated with solvent only. After completing the incubation periods, Regenolide-containing media was removed and all wells were washed with cold PBS. Next, 80 μl of RIPA lysis buffer with 1% protease inhibitor cocktail was added and incubated for 5 minutes at 40-degrees Celsius. The cells were harvested and crude lysate was collected in pre-chilled 0.5 ml Eppendorf tubes. Each sample was then sonicated for 30 seconds using an ultrasonicator and centrifuged for 10 minutes at 12,000 rpm. The supernatant was then collected and used for total protein quantification using a commercially-available BioRAD DC protein assay kit.

Western blot analysis was then performed. More particularly, 15 μg of total protein per sample was loaded on a 7.5% acrylamide gel (BioRAD Acrylamide Kit) and run for 50 minutes at a constant 60 mAmp and 275 V-hour. The samples were then transferred to a nitrocellulose membrane (GE Healthcare LifeScience) in a wet transfer method at constant 350 mAmp for 1.15 hours. The membranes were blocked in 2.5% BSA in TTBS blocking solution (Sigma-Aldrich) for 1 hour. Rabbit polyclonal primary antibodies for β-Catenin (0.22 μg/ml) (Abcam), TERT (1:1000) (Sigma-Aldrich), mTOR (2:1000) (Kinexus Bioinformatics), and GAPDH (1:1000) (Abcam) were used to incubate the blots overnight at 40-degrees Celsius on a rocking platform. On the next day, all primary antibody solutions were removed and blots were washed with TTBS to remove excess unbound primary antibodies and probed with goat anti-rabbit secondary antibody (1:10,000) for 1 hour at room temperature. The blots were then stained with western horseradish peroxidase (HRP) substrate (Millipore, Sigma) for 1 minute and subsequently imaged using a gel scanner (BioRAD). Quantity OneR software was used to quantify individual band intensities for each sample and represented as a ratio of target protein expression normalized to the GAPDH (loading control) of each sample.

Figure 22:
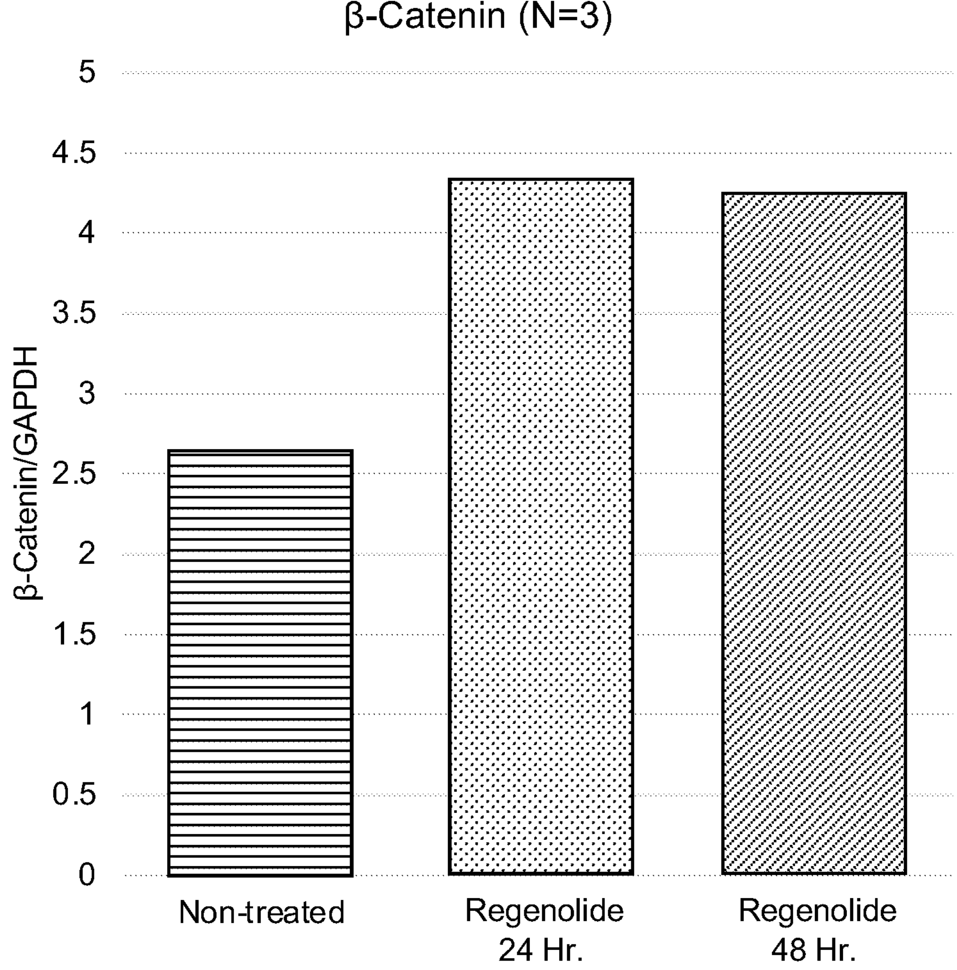
FIG. 22 is a bar graph showing the effects of the Ashwagandha/Withanolide-enriched compositions of the present invention (Regenolide) (at 1 μg/ml for 24 hours and 48 hours) on β-Catenin expression in HFDPC cells.
Figure 23:
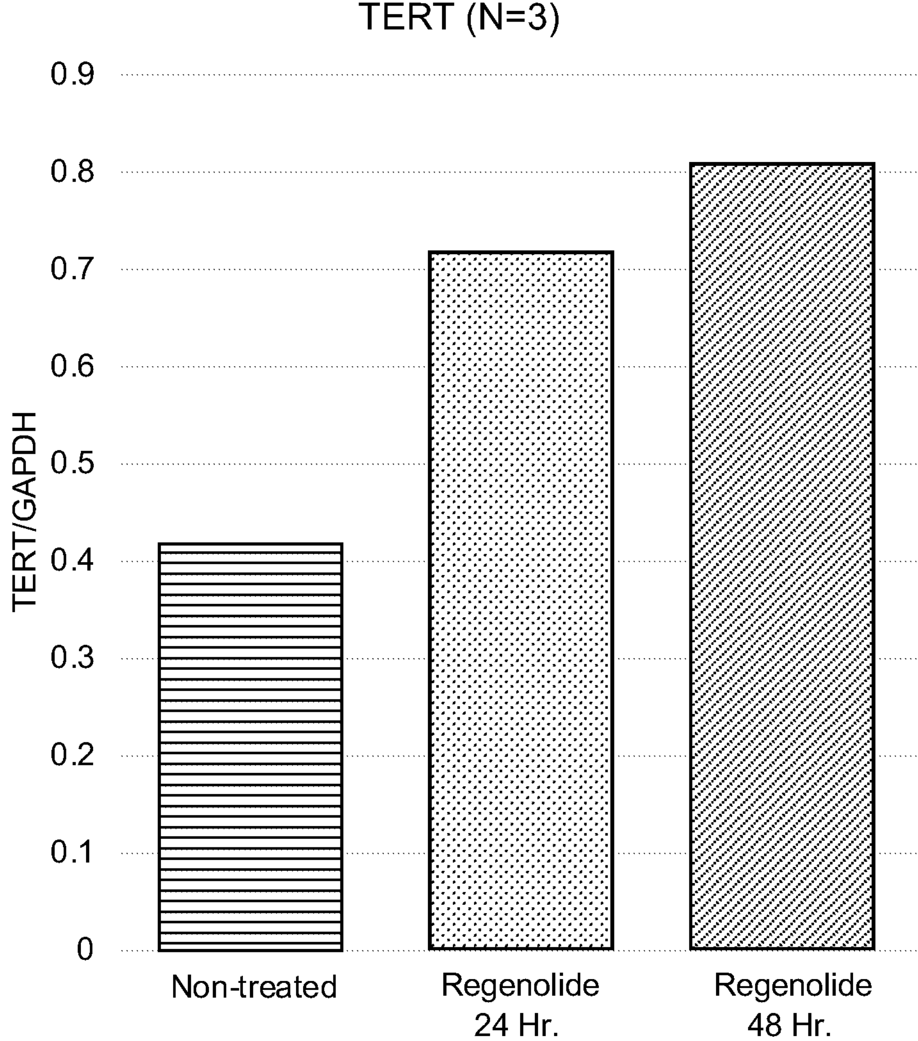
FIG. 23 is a bar graph showing the effects of the Ashwagandha/Withanolide-enriched compositions of the present invention (Regenolide) (at 1 μg/ml for 24 hours and 48 hours) on TERT expression in HFDPC cells.
Figure 24:
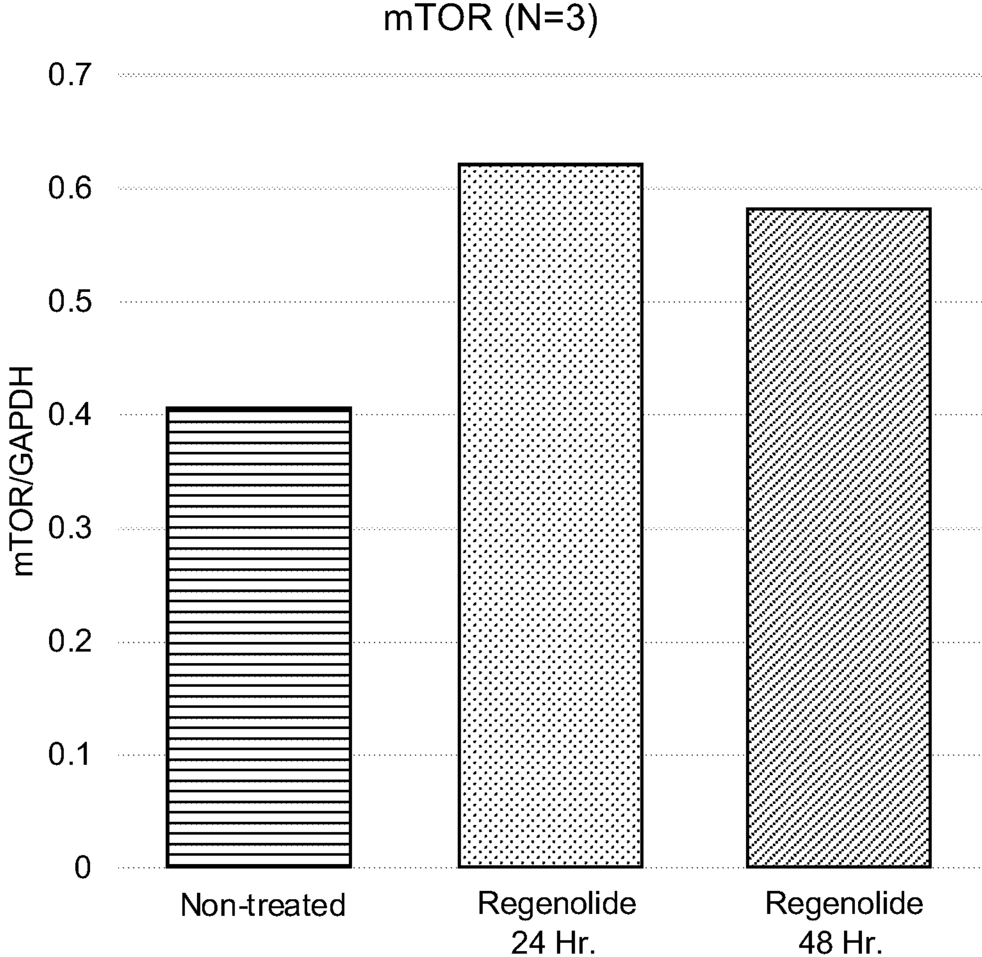
FIG. 24 is a bar graph showing the effects of the Ashwagandha/Withanolide-enriched compositions of the present invention (Regenolide) (at 1 μg/ml for 24 hours and 48 hours) on mTOR expression in HFDPC cells.

As shown in FIGS. 18-24, Regenolide-treated HFDPC cells exhibited dose- and time-dependent increases in β-Catenin, TERT (Telomerase Reverse Transcriptase), and mTOR expression as compared to non-treated control cells. Importantly, the results showed that β-Catenin (FIG. 19), TERT (FIG. 20), and mTOR (FIG. 21) expression in HFDPC cells was elevated after treatment with Regenolide at 0.5 μg/ml and 1 μg/ml for 24 hours. Still further, the expression of β-Catenin, TERT, and mTOR was elevated in such HFDPC cells after treatment with Regenolide at 1 μg/ml for 24 and 48 hours (FIGS. 22, 23, and 24, respectively).

This Example 8 demonstrates the significant changes in biomarkers associated with human hair follicle dermal papilla cell (HFDPC) metabolism. Treatment with the Regenolide compositions of the present invention was found to increase β-Catenin and mTOR expression, indicating incremental subcellular activity associated with hair growth and general metabolic activation. Induction of β-Catenin activity or expression is recognized as a mechanism that leads to expression of pluripotent factors and ultimately anagen hair cycle induction and folliculogenesis. Likewise, the serine/threonine protein kinase, mTOR, is well known to regulate cell growth and cell proliferation, protein synthesis, autophagy and transcription. In addition, this Example 8 demonstrates that the Regenolide compositions can be applied to generate a time- and dose-dependent increase in TERT (Telomerase Reverse Transcriptase) activity, providing further support for the conclusion that Regenolide treatment induces rejuvenation and restoration of cell state, thereby setting the stage for hair restoration.

Example 9: Capsule Formulations

The following provides a few non-limiting examples of the Withanolide-enriched Ashwagandha compositions of the present invention, which are formulated and packaged as human-consumable capsules. The AshWITH-3 component referenced in the three examples below is an Ashwagandha natural extract supplemented with additional Withaferin A, which includes up to (but no more than) 1.5% (w/w) Withaferin A and not less than 12% (w/w) total Withanolides—as measured by gravimetric HPLC. More particularly, the AshWITH-3 component referenced in the three examples below is an Ashwagandha natural extract supplemented with additional Withaferin A, which includes approximately 1.5% (w/w) Withaferin A and approximately 12% (w/w) total Withanolides.

Capsule A

| Component | Quantity (mg) | Component Name |
|---|---|---|
| 1 | 200 | AshWITH-3 |
| 2 | 150 | Dry Maltodextrin* |
| 3 | 3 | Magnesium Stearate |
| 4 | 2 | Silicon Dioxide |
| Total | 355 | |

*Can be replaced with rice hull powder.

Capsule B

| Component | Quantity (mg) | Component Name |
|---|---|---|
| 1 | 200 | AshWITH-3 |
| 2 | 50 | Dry Maltodextrin* |
| 3 | 300 | n-Acetylcysteine |
| 4 | 4 | Magnesium Stearate |
| 5 | 3 | Silicon Dioxide |
| Total | 557 | |

*Can be replaced with rice hull powder.

Capsule C

| Component | Quantity (mg) | Component Name |
|---|---|---|
| 1 | 200 | AshWITH-3 |
| 2 | 65 | Dry Maltodextrin* |
| 3 | 170 | L-Tryptophan |
| 4 | 100 | Valerian Root |
| 5 | 20 | Passion Fruit Extract |
| 6 | 4 | Magnesium Stearate |
| 7 | 3 | Silicon Dioxide |
| Total | 562 | |

*Can be replaced with rice hull powder.

The many aspects and benefits of the invention are apparent from the detailed description, and thus, it is intended for the following claims to cover all such aspects and benefits of the invention, which fall within the scope and spirit of the invention. In addition, because numerous modifications and variations will be obvious and readily occur to those skilled in the art, the claims should not be construed to limit the invention to the exact construction and operation illustrated and described herein. Accordingly, all suitable modifications and equivalents should be understood to fall within the scope of the invention as claimed herein.

What is claimed is:

1. A method for increasing expression of β-Catenin and/or mammalian target of rapamycin (mTOR) in a group of cells by providing said group of cells with an effective amount of a composition, wherein the composition comprises an extract of *Withania somnifera* and Withaferin A is added to said extract, such that the composition includes at least 20% (w/w) Withaferin A.

2. The method of claim 1, wherein Withaferin A is added to said extract, such that the composition includes at least 25% (w/w) Withaferin A.

3. The method of claim 1, wherein all Withanolides in the composition constitute at least 35% (w/w) of the composition.

4. The method of claim 1, wherein the composition is formulated for topical scalp or skin application and is combined with one or more essential oils; one or more pharmaceutically acceptable carriers; or a combination of such essential oils and pharmaceutically acceptable carriers.

5. The method of claim 4, wherein the pharmaceutically acceptable carriers are selected from the group consisting of alcohols, propylene glycol, water, and surfactants.

* * * * *